(12) United States Patent
Neoh et al.

(10) Patent No.: US 11,285,297 B2
(45) Date of Patent: Mar. 29, 2022

(54) CATHETER DEVICES WITH VALVES AND RELATED METHODS

(71) Applicant: B. Braun Melsungen AG, Melsungen (DE)

(72) Inventors: Boon Ping Neoh, Penang (MY); Jarryd Keng Gene Ng, Penang (MY)

(73) Assignee: B. Braun Melsungen AG, Melsungen (DE)

( * ) Notice: Subject to any disclaimer, the term of this patent is extended or adjusted under 35 U.S.C. 154(b) by 380 days.

(21) Appl. No.: 16/344,746

(22) PCT Filed: Oct. 20, 2017

(86) PCT No.: PCT/EP2017/076856
§ 371 (c)(1),
(2) Date: Apr. 24, 2019

(87) PCT Pub. No.: WO2018/077748
PCT Pub. Date: May 3, 2018

(65) Prior Publication Data
US 2019/0262586 A1   Aug. 29, 2019

Related U.S. Application Data

(60) Provisional application No. 62/413,769, filed on Oct. 27, 2016.

(51) Int. Cl.
*A61M 25/06* (2006.01)
*A61M 5/00* (2006.01)
(Continued)

(52) U.S. Cl.
CPC ...... *A61M 25/0618* (2013.01); *A61M 5/3273* (2013.01); *A61M 25/0097* (2013.01);
(Continued)

(58) Field of Classification Search
CPC .......... A61M 25/0618; A61M 25/0097; A61M 25/0693; A61M 39/06; A61M 5/3273; A61M 2207/00
See application file for complete search history.

(56) References Cited

U.S. PATENT DOCUMENTS 5,954,698 A    9/1999  Pike
2004/0193110 A1  9/2004  Giambattista et al.
(Continued)

FOREIGN PATENT DOCUMENTS

CN    101244300 A    8/2008
CN    104174099 A    12/2014
(Continued)

OTHER PUBLICATIONS

International Preliminary Reporton Patentability (Chapter I) on corresponding PCT application (PCT/EP2017/076856) from International Searching Authority (EPO) dated May 9, 2019.
(Continued)

*Primary Examiner* — Lauren P Farrar
*Assistant Examiner* — Hamza A Darb
(74) *Attorney, Agent, or Firm* — Klein, O'Neill & Singh, LLP

(57) ABSTRACT

Needle assemblies, such as catheter devices, and related methods having a needle hub with a needle, a catheter tube with a catheter hub and having the needle extending through the catheter tube. A valve is positioned in an interior cavity of the catheter hub and a valve actuator having an extension leg with an engagement section for supporting an arm of a needle safety clip when the safety clip is located in the interior cavity of the catheter hub.

25 Claims, 14 Drawing Sheets

(51) Int. Cl.
*A61M 5/32* (2006.01)
*A61M 39/06* (2006.01)
*A61M 25/00* (2006.01)

(52) U.S. Cl.
CPC ........ *A61M 25/0693* (2013.01); *A61M 39/06* (2013.01); *A61M 2207/00* (2013.01)

(56) References Cited

U.S. PATENT DOCUMENTS

| | | |
|---|---|---|
| 2008/0039802 A1 | 2/2008 | Vangsness et al. |
| 2008/0108944 A1 | 5/2008 | Woehr et al. |
| 2015/0151085 A1* | 6/2015 | Tan ................. A61M 5/321 604/164.08 |

FOREIGN PATENT DOCUMENTS

| | | |
|---|---|---|
| CN | 105451803 A | 3/2016 |
| EP | 2343095 A1 | 7/2011 |
| EP | 2638926 A1 | 9/2013 |
| JP | 2016-509916 A | 4/2016 |
| WO | WO 2014/140265 A1 | 9/2014 |
| WO | WO 2015/082551 A1 | 6/2015 |
| WO | WO 2015/104336 A1 | 7/2015 |
| WO | WO 2016/142410 A1 | 9/2016 |

OTHER PUBLICATIONS

Office Action on corresponding foreign application (CN Application No. 201780081197.8) from the National Intellectual Property Administration, P.R. China dated Jan. 28, 2021.
International Search Report and Written Opinion on corresponding PCT application (PCT/EP2017/076856) from International Searching Authority (EPO) dated Jan. 25, 2018.
Office Action on corresponding foreign application (CN Application No. 201780081197.8) from the National Intellectual Property Administration, P.R. China dated Aug. 4, 2021.
Office Action on corresponding foreign application (JP Application No. 2019-522566) from the Japan Patent Office dated Jul. 27, 2021.
First Examination Report on corresponding foreign application (IN Application No. 201917013890) from the Indian Patent Office dated Jul. 28, 2021.

* cited by examiner

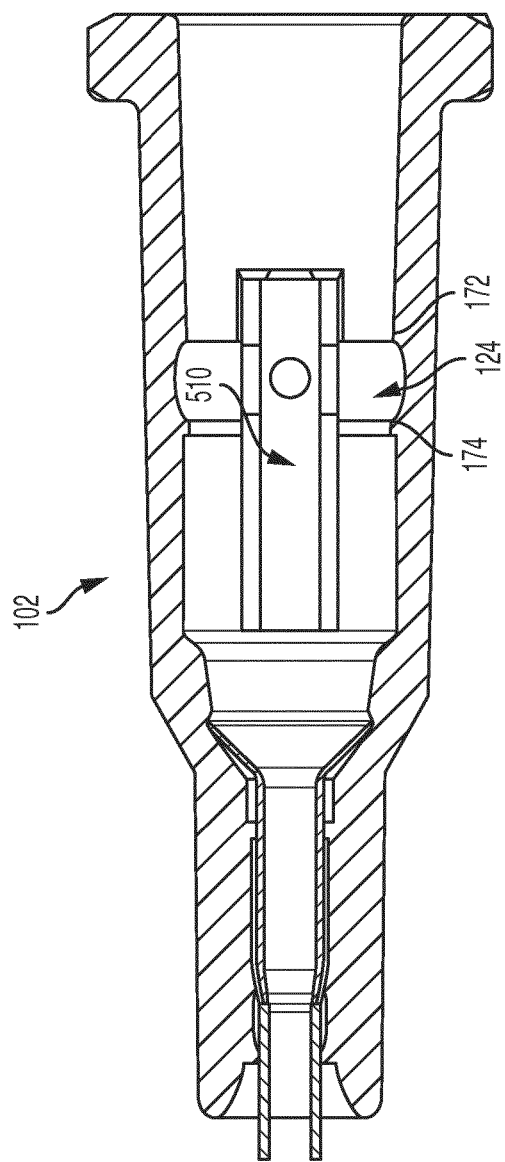

CATHETER DEVICES WITH VALVES AND RELATED METHODS

FIELD OF ART

The disclosed invention generally relates to needle devices and intravenous (IV) infusion devices, including IV catheters. In particular, IV catheter assemblies having a valve and a valve actuator for opening the valve are disclosed.

BACKGROUND

IV catheters are commonly used for a variety of infusion therapies, including infusing fluids into a patient, withdrawing blood from a patient, or monitoring various parameters of the patient's vascular system. Catheters are typically connected to a catheter adapter that accommodates the attachment of IV tubing to the catheter. Blood control catheters include an internal blood control valve that is opened by the insertion of a male Luer or other object into a proximal end of the catheter adapter. Non-limiting examples of blood control valves are disclosed in United States Patent Application Publication No. 2011/0046570, filed Aug. 20, 2009, titled "Systems and Methods for Providing a Flushable Catheter Assembly." Following placement of the catheter into the vasculature of a patient, an IV fluid source can be connected to the catheter adapter or catheter hub, opening the blood control valve. Thus connected, fluid from the IV source can begin flow into a patient through the catheter.

As is well known in the art, typical blood pressure is 10 to 20 centimeters of water. Infusion bags are usually placed about 100 cm above the patient's heart to direct flow into the patient. At roughly that height, the pressure exerted by the fluid from the infusion bag is much greater than the blood pressure of the patient and therefore can flow into the patient.

Some catheter adapters permit verification of proper placement of the catheter in the blood vessel before fluid infusion begins, such as by providing a flashback chamber of the catheter assembly where a "flashback" of blood can be observed. To confirm flashback in catheter assemblies that do not include a blood control valve, a clinician must manually occlude the vein to prevent undesirable exposure to blood. In contrast, blood control valves can eliminate the need for such manual occlusion, while also reducing the likelihood of blood exposure during catheter placement.

SUMMARY

Needle assemblies are disclosed, which can include over-the-needle catheter assemblies and safety intravenous catheter (IVC) assemblies. Methods of use and of making needle assemblies and their components form part of the present disclosure.

Aspects of the present disclosure include a needle assembly comprising a needle hub with a needle extending from a distal end of the needle hub; a catheter hub; a catheter tube attached to the catheter hub and having the needle extending through the catheter tube in a ready to use position; a valve positioned in an interior cavity of the catheter hub, said valve comprising a valve body having an outer perimeter positioned in a bore section of the catheter hub, a proximal receptacle on a proximal end, a distal receptacle on a distal end, and a valve disc located between the proximal and distal receptacles; an actuator positioned in the interior cavity of the catheter hub, the actuator is configured to open the valve, the actuator comprising: a rigid body on a distal end of the actuator, the rigid body having a nose section and an activation end located within the proximal receptacle and configured to push the valve disc to open the valve; and a first extension leg on a proximal end of the actuator, the first extension leg having a first engagement section for holding a first arm of a safety clip, the first engagement section configured to prevent dislodgement of the safety clip from the interior cavity of the catheter hub while in the ready to use position.

The safety clip can embody a needle guard. The needle guard can have many alternative features for covering or blocking a needle tip from inadvertent needle sticks. In an example, a needle guard can be sized and shaped to fit inside a catheter hub. For example, a needle guard can be located inside the catheter hub with a valve and a valve opener. In other examples, a needle guard can be a spring loaded device that propels a needle, via a spring action, into a protective barrel so that the needle tip is recessed within the protective barrel to be covered from inadvertent needle sticks.

Usable needle guards can be unitarily formed, such as by injection molding or by cold working a stamped metal sheet, or be assembled together using two or more separately formed sub-components.

The actuator can further comprise a radially extending tab formed on the extension leg located in an undercut formed on the interior surface of the catheter hub, the location of the radially extending tab in the undercut can prevent dislodgement of the actuator from within the interior cavity of the catheter hub.

The undercut can include a proximal shoulder and a distal shoulder and wherein the radially extending tab of an actuator can contact the proximal shoulder in a ready to use position.

The actuator can further comprise one or more guide arms extending radially from the actuator, the one or more guide arms can engage one or more slots formed axially on the interior surface of the catheter hub. The engagement can prevent rotation of the actuator within the catheter hub.

The actuator can further comprise a second extension leg on the proximal end of the actuator spaced from the first extension leg, the second extension leg can include a second engagement section for holding the first arm of the safety clip.

The actuator can further comprise a third engagement section formed on the first extension leg near the first engagement section and a fourth engagement section formed on the second extension leg near the third engagement section.

The extension legs can have linear or straight leg portions or can have curved portions extending from the body and then linear portions or straight portions along the axial direction. The two linear portions can have a gap therebetween.

Each plunger element or leg extension can have a round cross-section or a multi-sided cross-section, such as a polygonal shaped cross-section. The cross-section can optionally have an irregular shape.

The first engagement section can be formed opposite the second engagement section and the third engagement section can be formed opposite the fourth engagement section.

The first engagement section and fourth engagement section can be configured to engage with the first arm of the safety clip and the second engagement section and third engagement section can be configured to engage with a second arm of the safety clip, wherein the first arm and second arm can have different lengths.

The first engagement section can be formed on an inner surface of the extension leg and a second engagement section can be formed on the inner surface of the extension leg, diagonally to the engagement section.

The first engagement section can extend substantially across the extension leg.

The first extension leg and the second extension leg can be deflectable radially inwardly towards one another when actuated by a male medical implement.

The deflection of the two plunger elements can then space the two radial tabs from the interior surfaces of the catheter hub to then reduce drag or friction as the actuator is advanced in the distal direction by the male Luer tip.

Flexing of the plunger elements can move the outward protrusions away from the surfaces of the groove to minimize drag or friction as the actuator is advanced in the distal direction.

The nose section of the actuator can have a frusto-conical shape and the proximal receptacle of the valve can have a reverse frusto-conical surface. The frusto-conical shape of the nose section and the reverse frusto-conical surface of the valve can form a size-on-size fit.

The distal receptacle of the valve can have a dome surface. The dome shape receptacle is sized and shaped to accommodate expansion of two or more flaps of a valve disc.

A further aspect of the present disclosure is an actuator configured to be positioned in an interior cavity of a catheter hub, adjacent a valve, the actuator sized and shaped to move the valve axially and open the valve, the actuator comprising: a rigid body on a distal end of the actuator, the rigid body having a nose section and an activation end, the nose section sized and shaped to fit into a receptacle formed on the valve and open one or more slits on the valve when moved; a guide arm extending radially from the actuator, the guide arm configured to engage a slot formed axially on the interior surface of the catheter hub, the engagement configured to prevent rotation of the actuator within the catheter hub; and a first extension leg on a proximal end of the actuator, the first extension leg having a first engagement section for holding an arm of a safety clip, the first engagement section configured to prevent dislodgement of the safety clip from the interior cavity of the catheter hub while in the ready to use position.

The actuator can further comprise a radially extending tab formed on the extension leg, the tab can be configured to engage an undercut formed on the interior surface of the catheter hub, the engagement can prevent dislodgement of the actuator from within the interior cavity of the catheter hub.

The actuator can further comprise a second extension leg on the proximal end of the actuator, the second extension leg can have a second engagement section for holding the first arm of a safety clip.

The actuator can further comprise a third engagement section formed on the first extension leg near the first engagement section and a fourth engagement section formed on the second extension leg near the third engagement section.

The first engagement section can be formed opposite the second engagement section and the third engagement section can be formed opposite the fourth engagement section.

The first engagement section and fourth engagement section can be configured to engage the first arm of the safety clip and the second engagement section and third engagement section can be configured to engage a second arm of the safety clip, wherein the first arm and second arm can have different lengths.

The first extension leg and the second extension leg can each comprise a free end and wherein the two free ends are radially deflectable towards one another when pushed by a male medical implement.

The two free ends can move away from one another when the male medical implement is no longer abutting or contacting the actuator.

The actuator can remain engaged to a valve and opening one or more slits of the valve when the male medical implement is no longer abutting or contacting the actuator.

The first extension leg and the second extension leg can each comprise a weakened section configured to deflect.

The first engagement section can comprise a bump.

A still further aspect of the present disclosure is a method of manufacturing a needle assembly comprising: providing a catheter hub with a catheter tube with a distal opening, said catheter hub comprising a hub body defining an interior cavity and a proximal opening; positioning a bushing inside the catheter hub and against the catheter tube and positioning a valve proximal of the bushing; the valve comprising a valve body having a distal valve section and a proximal valve section defining a proximal receptacle, and wherein the distal valve section is located in a bore section of the interior cavity and the bore section contacts both the distal valve section and the proximal valve section to secure the valve in a distal direction; positioning a valve opener adjacent the valve and inside the interior cavity of the catheter hub so that a nose section of the valve opener is located inside the proximal receptacle, the valve opener comprising a first extension leg on a proximal end of the valve opener, the first extension leg having a first engagement section; positioning an arm of a safety clip over the first engagement section, the first engagement section configured to prevent dislodgement of the safety clip from the interior cavity of the catheter hub; placing a needle, which is attached to a needle hub, through the catheter hub, the valve, the valve opener, the safety clip and the catheter tube so that a tip of the needle extends out the distal opening of the catheter tube.

The catheter assembly described herein may more broadly be referred to as a needle assembly or a needle device. The assembly can comprise a catheter hub with a catheter tube attached to the catheter hub. Interiorly of the catheter hub, a septum or valve, an actuator and a safety clip, such as a needle guard or tip protector, can be provided.

A needle and needle hub can be inserted through the proximal opening of the catheter hub, with the needle tip protruding from the distal opening of the catheter tube.

The valve and valve actuator can remain with the catheter hub for controlling fluid flow therethrough after removal of the needle from the catheter hub. The actuator is configured to be pushed into the valve to open the valve for fluid flow.

The actuator can comprise a body, one or more extension legs or elongated extension members, and one or more guiding arms. The guiding arms can be referred to as guide arms.

The body of the actuator can be rigid or semi rigid. The body can be configured to engage with the valve to open the valve as an axial force is applied to the actuator towards the distal end of the catheter assembly, such as during the insertion of a male Luer.

Generally, the body of the actuator is rigid relative to the more pliable valve, which allows the body, such as the nose section of the actuator with the activation end, to actuate the valve, such as to deflect at least part of the valve to open the valve for fluid communication between a region distal of the valve and a region proximal of the valve. For example, the body of the actuator can be made of a non-compressible material, such as metal, or a somewhat compressible material such as a hard elastomer. A rigid plastic material may also be used to form the actuator, such as a polycarbonate material.

In some examples, the activation end of the actuator can have a groove or a catch section to engage the valve for use as a one-time opening of the valve without re-use. With the groove or catch section, the actuator can remain engaged to the valve after removal of the male Luer tip.

In an example, a male Luer tip can be inserted into the proximal opening of the catheter hub after removal of the needle to then push the actuator distally into the valve to open the valve. The proximal opening of the catheter hub should be exposed after removal of the needle and needle hub to then receive the male Luer tip.

In still other examples, the valve can have sufficient elasticity and the valve opener, such as the activation end of the valve opener, can be sized and shaped to allow the flaps to uncoil and for the valve opener to be pushed in the proximal direction by the valve to close the flaps from fluid flow. To again open the valve, the male Luer tip can be re-inserted into the catheter hub to advance the valve opener into the valve to open the flaps.

The actuator can be co-molded or insert molded and have an integrated structure made from two or more different materials.

The extension legs present a structure for a male Luer tip to push against. The extension legs may have one or more bumps or engagement sections or segments on each leg for engaging one or more arms of the safety clip, which can prevent dislodgement of the safety clip from the interior cavity of the catheter hub while in the ready to use position. Optionally, the needle assembly may be practiced without a safety clip.

Two end surfaces of a safety clip, such as ends of two distal walls, can engage the one or more bumps on the extension legs in a ready to use position instead of pressing against a side of the needle and against the interior of the catheter hub. While embodiments of the engagement sections or segments on the extension legs comprise bumps, other embodiments can comprise undercuts, notches, protrusions, ridges or other features that can engage with an arm or arms of the safety clip.

The one or more guiding arms extending radially of the actuator can engage one or more corresponding number of slots formed axially on the interior surface of the catheter hub to prevent rotation of the actuator as the actuator is advanced distally during activation. The length of the slots can be greater than the distal travel of the one or more guiding arms.

In a ready position with the needle hub in contact with the catheter hub and the needle tip extending out the distal end or distal opening of the catheter tube, the catheter assembly is ready for use, such as to perform a venipuncture or intravenous access. Sometimes the ready position first requires removing a protective cap from the catheter assembly or needle assembly 100 to expose the needle tip.

A flash back plug can be provided at the proximal end of the needle hub, which is removable from the needle hub and allows air to vent into the flash back chamber but stops blood from spilling out the proximal end when entering the flashback chamber during primary flashback. The needle hub can comprise a shoulder, tab, or other surfaces that physically contact the catheter hub, such as the proximal end surface of the catheter hub, to axially register the two hubs to set the length of the needle tip projecting out of the distal opening of the catheter tube.

Interiorly of the catheter hub, in the interior cavity, a safety clip or tip protector, a valve opener or actuator, a septum or valve, and a bushing can be provided. Optionally, the safety clip or tip protector can be omitted or can be located outside if the catheter hub, in a separate guard housing. The proximal opening of the catheter hub can be sized with a female Luer taper to receive a male Luer tip. The bushing ca be configured to wedge the proximal end of the catheter tube against the interior wall surfaces of the catheter hub to retain the catheter tube to the catheter hub.

The safety clip or tip protector may embody any number of prior art guards configured for blocking the needle tip of the needle. In an exemplary embodiment, the tip protector can embody one of the guards shown in U.S. Pat. No. 6,616,630, the contents of which are expressly incorporated herein by reference. The tip protector can have a proximal wall and two resilient arms each with a distal wall and wherein a change in profile on the needle, such as a crimp or a bulge, can engage a perimeter defining an opening on the proximal wall of the tip protector to retract the tip protector in the proximal direction out of the catheter hub following successful venipuncture.

The two arms can intersect when viewed from a side or they can run along different sides of the needle and do not intersect along the side view. In one embodiment, the needle guard arms can spread by the actuator in a ready position and not by the needle shaft and the spreading of the arms can force the arms to engage the inside of the catheter hub, such as the guard engagement section (e.g., an undercut or groove) of the catheter hub. In some example, the arms of the needle guard are spread by the actuator but the arms do not engage the interior of the catheter hub in the ready to use position.

In another example, the radial outermost surfaces of the arms, such as the elbows between the arms and the distal walls, do not engage or contact the interior of the catheter hub when the arms are spread by the actuator. Because the arms do not rest on the needle but rather on the bumps of the actuator in the current embodiment, the needle guard is therefore retained inside the interior of the catheter hub by the engagement with the bumps and not the catheter hub. For example, a gap can be provided between each outermost surfaces of the needle guard and the interior of the catheter hub when the arms engage the bumps of the actuator.

During retraction of the needle following use, the needle guard can be retained inside the catheter hub by the engagement between the arms and the bumps on the actuator. As the needle is withdrawn following use and a crimp on the needle engages the proximal wall of the tip protector, the elbow of an arm of the tip protector, if one arm or two elbows on two arms of the tip protector, can deflect outwardly into the space provided by the gaps or can flatten out if in contact with the catheter hub, such as against an edge of the guard engagement section of the catheter hub and against the valve actuator, causing the arms to move and release from the one or more bump on the one or more extension leg of the actuator.

The valve opener in accordance with aspects of the present disclosure can comprise a body with a nose section, one or more extension legs or plunger elements (e.g., such as a leg element or elongated extension), and one or more guiding arms.

The nose section of the body can be elongated and can have a passage or bore passing through the nose section. The bore at the nose section can provide a pathway for fluid flow and can accommodate a needle in a ready to use position of the catheter assembly.

The actuator or opener can have a lengthwise axis, the one or more guiding arms can extend radially relative to the lengthwise axis, and the one or more extension legs can extend axially or parallel to the lengthwise axis.

The extension legs can extend axially from the body. The extension legs can extend in a proximal direction. A gap can be provided between the two extension legs. A flange can be located at an end of each extension leg to provide abutting surfaces for a male Luer tip, as further discussed below.

In a particular example, two guiding arms can be provided and be diametrically opposed to one another along the lengthwise axis of the actuator. The guiding arms can extend from the body and each embody a rectangular or square structure having a generally straight or flat outer most edge, which can optionally be curved, undulating, serrated, or arc-shape.

The rigid body can have an elongated shape, such as a cylindrical shape, forming an activation end that can embody a ring shaped structure at the distal end. The elongated body can optionally have a draft angle or an inward taper in the distal direction. In operation, the activation end can press into a valve, when pushed distally by a male medical implement, such as a syringe tip, a Luer adapter, or an IV line, to actuate the valve.

In the ready position, the activation end may be in contact with the valve but may be spaced from the proximal surface of the valve disc. Optionally, the activation end can be in contact with the proximal surface of the valve disc prior to activation by a male Luer tip.

The activation end can be fitted into a receiving space of the valve, such as the proximal receptacle of the valve, and in contact with the valve, such as with the bore of the receiving space and/or the valve disc, as further discussed below.

Two plunger elements can extend from the rigid body in the proximal direction and each having a length measured in a lengthwise direction of the catheter assembly and a width, measured orthogonally to the length. Other embodiments may use one or three or more leg extensions or plunger elements extending from the rigid body.

In an embodiment, each plunger element is sized and shaped for contact by a male Luer to transfer a distally directed force from the male Luer, through the nose section, to the activation end to then open the valve. The overall length of the valve opener, hence the one or more plunger elements, can be selected so that insertion of a male Luer tip into the female Luer of a catheter hub is sufficient to push against the proximal end of the valve opener to axially move the valve opener into the valve to open the one or more flaps of the valve for fluid flow.

In an example, the leg extensions or plunger elements are flexible and deflectable so that when pushed by a male Luer tip, the plunger elements defect or flex. The plunger elements are deflectable by selecting a material that has the requisite resilient properties. In other examples, the plunger elements are deflectable by incorporating one or more weakened sections, such as by incorporating a structurally thin section, by incorporating cut-outs, by employing a small cross-section compared to other sections of the same elongated plunger element, or combinations thereof. Alternatively, the plunger elements can be flexible and deflectable by selecting a material that has the requisite resilient properties and by incorporating one or more weakened sections.

The plunger elements can each have an arc shape or arc cross section along a width of the actuator, similar to a crescent moon. In another example, each plunger element can be generally flat or planar along a cross section. In still other examples, each plunger element has more than one different cross-sectional profiles or contour along a length section.

An elongated plunger element can have a square profile located adjacent a crescent-shaped profile. In an embodiment, the thickness of each of two plunger elements is sufficiently small or thin so that the needle guard and the two plunger elements have sufficient clearance to fit within the interior cross-sectional space of the catheter hub without being physically binding against the catheter hub and rendered unmovable or fixed.

In an example, the thickness of each of two plunger elements and the width of the needle guard are such that no undercut or channel is required to be formed in the interior wall surfaces of the catheter hub to accommodate them. When the plunger element has an arc cross section, it can be mechanically stronger to take a greater load when being pushed by a male tip to push the activation end against the valve. This can allow a thin and compact design to be used for the infusion device and gives more room in the standardized space of a female Luer taper.

The valve opener can be made from a metal material or from a plastic material or from both. When made from a metal material, the valve opener can be formed by deep draw methods and the arc shape cross section of the plunger element can provide added rigidity when pushed by the male Luer. Each plunger element can comprise at least two lengthwise edges and a rib can be provided along one or both of the lengthwise edges to further add structural rigidity.

One or more gaps can be provided between any two plunger elements. The gaps can provide clearance or space for fluid flow flowing thereacross, such as during IV infusion. The gap can also be utilized to accommodate a needle guard.

The rigid body of the valve opener can comprise an exterior surface defining an outer perimeter and an interior surface defining a cavity. In an example, the outer perimeter can be generally cylindrical. In other examples, the outer perimeter can have a taper and can optionally include surface features such as bumps or grooves. Interiorly, the body can comprise a bore and openings at each end of the bore.

The body of the actuator or valve opener can have a continuous surface with no gaps or slots or with gaps/slots to facilitate fluid flow. The distal edge or intersection of the activation end and the outer perimeter can have a sharp edge or a blunt edge. In an example, the intersection can be a blunt edge comprising a planar surface for pushing against the valve.

On the proximal side of the rigid body of the actuator, two plunger elements can extend outwards in the axial proximal direction as well as radially from the outer perimeter to form a shoulder. In other words, the leg extensions can each have a curve or a bend. Said differently, the outer perimeter can have an outside diameter of a first dimension and the two plunger elements can define an outside diameter of a second dimension, which is larger than the first dimension. A shoulder can be provided between the two different dimensions.

One or more bumps may be formed on an interior surface of the leg extension or plunger elements. In some examples, one or more bumps or engagement sections can be formed on each leg extension, such as on the inside surface of each leg, at the gap between the two leg extensions. In other words, relative to a lengthwise axis of the actuator, the plunger element can have an interior surface closer to the lengthwise axis and an exterior surface further away from the lengthwise axis. The bumps can be configured to engage with one or more arms of the safety clip or tip protector, which can prevent dislodgement of the tip protector from the interior cavity of the catheter hub while in the ready to use position.

The one or more bumps can serve as mounting surfaces for the ends of the two arms of the tip protector, such as for the ends of distal walls of the arms, to rest thereon instead of against the needle shaft. This can help to decrease drag during retraction of the needle following successful venipuncture as there is no contact between the needle shaft and the ends of the two arms when the ends are rested on the bumps. When rested on the bumps, or engagement sections or segments, the needle guard can also contact the interior of the catheter hub or be spaced from the interior of the catheter hub.

In the illustrated embodiment, there can be two pairs of bumps opposite each other on the two opposite plunger elements. Each pair of bumps can be at a different distance from the proximal ends of the plunger elements, with one pair closer to the proximal edge and one pair farther from the proximal edge. The different distances can allow each pair of bumps to engage different length arms of the tip protector, which can be staggered in the axial direction.

Two bumps on each plunger element can be diagonally formed on the interior surface of the plunger element to allow a top arm of the tip protector to engage with a top bump and a bottom arm of the tip protector to engage with a bottom bump.

One pair of bumps can support an end of one distal wall of a needle guard and the other pair of bumps can support an end of the other distal wall.

Each pair of bumps can comprise a first bump and a second bump. The two bumps can be positioned along different planes or elevations to define two different surfaces for supporting two different ends on two different arms of a needle guard.

One bump can support one end of a distal wall so that the two bumps are configured to support the two ends of the two distal walls, one end on each distal wall.

One bump can support one end of a distal wall so that the two bumps on one plunger element are configured to support the two ends of the two distal walls, one end on each distal wall.

A first set of bumps and second set of bumps can at different distance axially along the plunger element. A long arm of the tip protector can engage with a first set of bumps and a short arm of the tip protector can engage with a second set of bumps. In some examples, only one first bump and one second bump are used to support the ends of the tip protector. The two single first and second bumps can be located separately on the two leg extensions so that one bump is on one of the leg extensions and another bump is on the other leg extension.

In some examples, the bumps can be provided with inclined surfaces or ramps to facilitate radial outward movement of the two arms as the crimp on the needle pulls on the proximal wall of the needle guard in the proximal direction.

The proximal end of a plunger element can form an outward protrusion or an outward protrusion can be incorporated at a proximal end of a plunger element. The outward protrusion can engage an undercut or groove formed on the interior surface of the catheter hub in order to help maintain the position of the actuator within the hub cavity.

Two outward protrusions on the two plunger elements can have planar surfaces that are generally orthogonal to the lengthwise axis of the actuator. Each of the two outward protrusions can provide a physical barrier for a male medical implement to push against to advance the actuator against the valve to open the valve. In other examples, the outward protrusions can be omitted where the cross section of the plunger elements are sufficiently large to be contacted by the male medical implement.

When incorporated, each outward protrusion can have a cross-section that is larger than the cross-section of the corresponding plunger element. In other examples, each outward protrusion can have a smaller cross section than the cross section of the plunger element but is strategically placed at the proximal end of the plunger element so as to be contacted by the male medical implement during activation. Optionally, only one outward protrusion is incorporated on one of the two plunger elements to both serve to angularly align the actuator to the interior surface of the catheter hub and to take the load of the male medical implement.

The outward protrusions on the two plunger elements can be configured to move in a groove inside the catheter hub between a proximal shoulder and a distal shoulder of the groove. The groove may be viewed as an undercut formed in or on the interior surface of the catheter hub forming or having a proximal shoulder and a distal shoulder.

In the ready to use position of the catheter assembly, the outward protrusions can abut the proximal shoulder of the groove while the nose section of the actuator can contact the valve to maintain a positive engagement between the actuator and the valve without opening the one or more slits on the valve. In an example, a nose section of the actuator is located in a proximal bore of the valve and in contact with the proximal shoulder of the groove inside the catheter hub.

In an activation position in which the actuator is advanced distally within the bore of the catheter hub, the outward protrusions can contact the distal shoulder of the groove inside the catheter hub. When contacted with the distal shoulder of the groove, the two plunger elements can be deflected inwardly due to the abutment or contact to assist with flexing the two plunger elements. In an example, when the two plunger elements are flexed during activation, they move radially closer together. When the male Luer tip is retracted away from the plunger elements, the two plunger elements can move radially further away from one another.

The present valve opener or actuator is understood to include abutting proximal surface or surfaces on the two plunger elements that are sized and shaped to be pushed against by a male Luer tip or a syringe tip when said tip is inserted into the proximal opening of the catheter hub following successful venipuncture to push the valve opener distally to open the valve.

The outward protrusions having the abutting surfaces may be referred to as radially extending tabs. The radially extending tabs can extend from the plunger elements. One or more than one radially extending tabs can extend from each plunger element. The radial extending tab or tabs can be located at a proximal most end or point on each plunger element.

Each of the two outward protrusions or radially extending tabs can provide a physical barrier for a male medical implement to push against to advance the actuator against the valve to open the valve.

The radial extending tabs can provide barriers to prevent a needle guard or safety clip from dislodging out of catheter hub when in a ready to use position. In an example, the needle guard is retained by the radially extending tabs during needle retraction but before proximal movement of the proximal wall by a change in profile or crimp located on the needle.

Two plunger elements can be pushed distally and can flex or deflect towards one another when pushed in the distal direction. The two plunger elements can deflect when pushed distally by a Luer tip and move closer to one another when no longer abutted by a male Luer tip.

A valve can be located inside a catheter hub just distal of the groove having proximal and distal shoulders and just proximal to the bushing. In some examples, the valve can touch the bushing. In other examples, the valve can be spaced from the bushing.

In an example, the valve comprises a valve body comprising a body diameter sized to seat within the catheter hub, and a valve disc having thickness measured orthogonal to the body diameter, and one or more slits defining two or more flaps formed through the thickness of the valve disc. For example, one or two or three slits may be provided through the valve thickness to define two to three flaps. In the illustrated embodiment, one slit extends through the center of the valve disc.

The valve can include a proximal valve section and a distal valve section. The proximal valve section can be provided with bore having a frusto-conical surface. The frusto-conical surface can be configured to engage with the activation end and part of the nose section of the rigid body of the actuator in a ready to use position. In some embodiments, the surface of the bore may be formed into other shapes and still function as a receptacle for the activator, such as an inverse cylinder or inverse rectangular or cubic box. The distal end of the bore is can be blocked by the valve disc, which can have one slit with two or more slits defining two or more flaps contemplated.

A valve or septum disclosed herein can include a distal valve section having an exterior surface and an interior surface defining a bore. A distal end edge can be provided between the interior and exterior surfaces. The bore of the distal valve section can comprise an inverse dome surface, such as a concave surface, formed on the distal side of the valve.

The dome surface can provide space for the valve to collapse into when a Luer tip is inserted into the catheter hub. In other words, the bore of the distal valve section can be provided with sufficient space to accommodate the expanding valve disc when the valve disc is pushed distally by a male medical implement or male Luer tip. This allows the valve and the actuator to remain engaged even after removal of the male medical implement used to advance the actuator into the valve.

Valves and septums disclosed herein can comprise a distal cavity and a proximal cavity. The distal cavity can have a dome shape or surface. The proximal cavity can have an inverse frusto-conical surface.

A valve disc comprising one or more slits defining two or more flaps can be located between the proximal and distal cavities of the valve. The proximal cavity can accommodate a nose section of an actuator and the distal cavity can accommodate expansion of the two or more flaps of the valve disc when the valve disc is pushed distally by the nose section of the actuator.

Three slits can originate from a point and extend radially from about a center point or central portion of the valve disc, similar to a three-point star, to form three flaps that can deflect along the slits.

The valve can comprise an outer perimeter that can float inside the interior cavity of the catheter hub, between the valve opener and the bushing. For example, the outer perimeter of the valve can move proximally and distally within the interior cavity of the catheter hub and not be restrained by the catheter hub along an axial direction of the catheter assembly. In an embodiment, at least some part or all of the distal edge or intersection of the activation end of the actuator is recessed from the outer perimeter of the valve so that the distal edge can abut or touch the proximally facing wall surface of the valve disc to open the valve disc, as further discussed below.

The distal valve section of the valve can be inserted into a bore section of the catheter hub, at the distal end of the interior cavity of the catheter hub. The distal valve section can be press fit into the bore section of the catheter hub and the blunt distal end of the valve can contact the bushing.

The intersection between the proximal and distal valve sections of the valve as well as the proximal and distal valve sections can seat against a corresponding shoulder or stepped surface formed in the interior cavity of the catheter hub to axially fix the valve within the catheter hub. In some examples, the distal end of the valve can be spaced from the bushing.

The valve can be positioned inside a single hub body catheter hub, such as by advancing the valve against an interior shoulder within the interior cavity of the catheter hub. In other words, the valve does not have to be retained inside a catheter hub by two or more catheter hub bodies, such as along a seam of two or more hub bodies. The outer perimeter of the valve can be larger than the interior diameter of the catheter hub so that the valve can be retained inside the catheter hub via a press fit.

The interior cavity of the catheter hub can include a groove, which can include a proximal shoulder and a distal shoulder. The outward protrusions on the two plunger elements can contact the proximal shoulder of the groove in the interior of the catheter hub to limit proximal movement of the actuator or activator.

At the distal end of the activator or actuator, the activation end and the nose section of the rigid body can project into the proximal bore of the proximal valve section and the actuator can be stopped from moving in the distal direction by the contact with the valve. In an example, the contour of the nose section, at least at the distal end of the actuator, and the bore of the proximal valve section can be the same or can be substantially the same, such as having a frusto-conical shape and an inverse frusto-conical shape, to provide a size-on-size fit. In other examples, the nose section and the bore can have dissimilar contours provided at least some parts of the two structures contact one another in the ready to use position prior to activation.

In an example, the nose section and the activation end of an actuator are located inside the bore of a valve in a size-on-size fit. In another example, the distal part of the rigid body, such as the nose section, is slightly larger than the bore of the valve so that the rigid body pre-loads the interior of the bore of the valve in the ready to use position.

The loading, size, and shape of the various components, such as the valve, the actuator, and the groove, can be selected so that while the actuator touches the valve in a ready to use position, the actuator does not open the one or more slits of the valve disc prior to activation. In other words, once the needle is retracted following successful venipuncture and the actuator is not activated by a male Luer tip, the valve is closed and no fluid, or at least no significant flow of fluid, passes between the region proximal of the valve and the region distal of the valve, or vice-versa even though the actuator can contact the proximal wall surface of the valve disc. Further, the contact relationships between the actuator and the groove of the catheter hub and between the actuator and the valve can limit potential proximal movement of the valve, either during retraction of the needle following successful venipuncture or following complete removal of the needle from the catheter hub.

Following catheterization, the needle tip can move proximally of two distal walls of a needle guard or tip protector, one on each end of the resilient arms. Alternatively, the needle guard can have one distal wall and/or one arm. As the two distal walls and hence the two resilient arms are pulled proximally by the needle, such as by the change in profile or crimp on the needle pulling on the perimeter defining the opening on the proximal wall of the needle guard, the two arms can move radially outwardly to disengage from the two guard engagement sections or bumps on the valve opener. Alternatively, the one arm and one distal wall disengage from the one guard engagement section.

When the needle continues to move in the proximal direction following use and the change in profile on the needle pulls on a perimeter on the proximal wall of the tip protector, the tip protector can moves proximally with the needle and then upon separating from the bumps, the two distal walls on the tip protector can close over the needle tip to a needle tip blocking position.

In an alternative embodiment, the needle guard can clamp onto the needle shaft without a crimp and be removed from the catheter hub as a unit. For example, a needle guard with two wall surfaces each with an opening can be used with a needle without a crimp such that when the needle guard is activated, the wall surfaces of the needle guard cant over so that the openings on the two walls clamp against the exterior of the needle shaft.

The valve can remain inside the interior cavity of the catheter hub following removal of the needle from the catheter hub. Thus, the valve can locate inside the catheter hub in both the ready position of the needle and the protective position of the needle.

Viewed from another perspective, the valve can be located inside the catheter hub in both the ready to use position of the catheter assembly, in which the needle tip projects out a distal opening of the catheter tube, and a protective position of the catheter assembly, in which the needle is removed from the catheter hub and the needle tip is covered by a tip protector.

One or more slots can be formed on the interior surface of the catheter hub. The one or more slots can form axially along the interior of the catheter hub and configured to engage with one or more guiding arms of the actuator. When engaged by a male Luer tip, the actuator can slide in the axial direction but is otherwise restricted from rotating by the one or more slots.

In an embodiment, two slots can be formed on opposite interior surfaces of the catheter hub and can be configured to engage two opposite guiding arms of the actuator. Other embodiments may use one, three, or more pairs of engaged slots and arms to prevent rotation of the actuator within the catheter hub. This can ensure that the actuator moves axially in the correct orientation to actuate the valve when a Luer tip is inserted into the catheter hub.

The one or more slots can intersect the groove having the proximal shoulder and distal shoulder. The groove is configured to abut a radial tab on a plunger element of an actuator.

A male medical implement can have a threaded collar for threaded engagement with the exterior threads on a catheter hub of the present disclosure. The threaded collar can be fixed to the male tip or be rotatable relative to the male tip. The male medical implement or instrument can be a male Luer, a syringe tip, an IV set connector, or other male tip having a Luer taper. For example, the male medical implement can be connected to an IV tubing, which can be connected to an IV fluid source for fluid delivery through the male medical implement, the catheter hub, and the catheter tubing to deliver fluid therapy to a patient.

When inserting a male medical implement or male tip into the proximal opening of a catheter hub of the present disclosure, the male tip initially contacts the plunger elements on the valve opener to advance a distally directed force on the two plunger elements to move the activation end distally forward into the valve to open the valve.

The arc cross section of each of the plunger elements can have a smaller diameter than the inside diameter of the catheter hub to provide a larger overlapping contact surface for the distal end of the male medical instrument to push against.

Outward protrusions or radial tabs on the two plunger elements of the actuator can provide ample proximal surfaces that are configured to be abutted by a male Luer tip without missing or misaligning during activation.

A distally directed force generated by a male Luer can move a valve opener in the distal direction until the geometries of the male tip and the proximal opening of the catheter hub stop further distal advancement of the male tip. In an example, a female Luer taper of the catheter hub and a male Luer taper of the male tip register and block distal advancement of the male tip further into the opening of the catheter hub. A seal is provided by the Luer engagement to prevent fluid from leaking out the proximal opening of the catheter hub.

As a valve opener or actuator moves distally by a distal advancement of a male tip, the activation end of the valve opener is urged distally and pushes against the proximally facing surface the valve disc of the valve. In particular, the activation end of the valve opener initially pushes against the proximally facing surface of the valve disc. For example, the activation end can contact and push on the proximally facing wall surface of the valve disc, causing the valve slit on the valve disc to open.

The valve body can be axially fixed, such as abutted against a distal shoulder or stepped surface provided in the distal bore section of the interior cavity of a catheter hub, and only the flaps of the valve disc deflect distally forward when pushed by an actuator to open the valve. In some examples, depending on the elasticity or rigidity of the valve body, the valve disc compresses between the tapered surface of the actuator and the interior wall surfaces of the catheter hub to open the slit for fluid flow. Part of the valve body can also deflect and/or compress by the male Luer tip during the activation process.

Once a valve is opened, fluid from a male tip can flow through the catheter hub, through the valve, and through the lumen of the catheter tube.

Alternatively, a suction can be generated by the male medical instrument, such as a syringe or vacuum blood collection tube, and blood aspirated from the patient. This can be performed for testing samples before infusion therapy is commenced. Also, any remaining blood can first be flushed from the inside of the catheter hub before infusion therapy is commenced.

The valves or septums described herein can be made of a pliable material, such as an elastomer, that is configured to deform and compress between the actuator, the interior surface of the catheter hub, and possibly part of the bushing. In an embodiment, the actuator can be configured to remain attached to the valve, in the distally forward position, even after the Luer tip is removed following an activation process. For example, the guiding arms of the actuator can engage undercuts or grooves on the interior catheter surface to lock the actuator into the forward position. In another example, the guiding arms can retain the actuator in the forward position due to frictional bias against the interior catheter hub surface. In still other examples, the compressive force generated by the tapered section of the rigid body of the actuator is greater than the recovery force generated by the resilient properties of the valve such that the valve actuator can remain in the distally forward position even after the male tip is removed.

In some examples, a biasing member, such as a helical spring or an elastomeric ring, may be placed distally of the valve, such as between the bushing and the valve, to assist the flaps in returning to their uncompressed or un-deflected state to close the one or more slits.

When a male Luer tip advances an actuator in a distal direction, the distal end surface of the male Luer tip pushes against the proximal surfaces of one or more outward protrusions or radial extending tabs. In an example, the proximal surfaces are not orthogonal to the lengthwise axis of the actuator so that when pushed by the planar surface of the male Luer tip, the contact causes the two elongated elements to which the two outward protrusions are attached to deflect radially inwardly towards one another.

Alternatively or additionally thereto, as the two outward protrusions move distally forward within the groove inside the interior cavity of the catheter hub, the two outward protrusions can contact a distal shoulder of a groove formed in the interior of the catheter hub, the geometry of which causes the two outward protrusions to deflect radially inwardly, which causes the two elongated elements to deflect radially inwardly towards one another.

In an example, the radial inward deflection of two elongated elements of an actuator towards one another during distal displacement by a male Luer tip allows the actuator to move an axial distance that is greater than the length measured between the proximal shoulder and the distal shoulder of the groove inside the catheter hub. In other words, the deflection of the two plunger elements radially inwardly make room, such as provide clearance, for the actuator to move in the distal direction. The overall length of the valve actuator, hence the one or more plunger elements, can be selected so that insertion of a male Luer tip into the female Luer of a catheter hub is sufficient to push against the proximal end of the valve actuator to axially move the valve actuator into the valve to open the one or more flaps of the valve for fluid flow.

The deflection between the outward protrusions on the two leg extensions or elongated elements and the distal shoulder of the groove on the interior surface of the catheter hub enables the actuator, hence the male Luer tip, to move distally until the male Luer tip and the female Luer of the catheter hub register. Thus, even if the outward protrusions of the actuator contact the distal shoulder prior to the two Luer surfaces register or seat, the physical barrier can still be overcome since the two elongated elements can deflect radially inwardly towards one another.

The male Luer tip can still advance distally when the outward protrusions of the actuator contact the distal shoulder of the groove until the male Luer tip is seated within the female Luer as the elongated elements can deflect radially inwardly when pushed against the distal shoulder so that any physical barrier experienced by the contact can be overcome.

Upon removal of the male Luer tip, the actuator can remain engaged to the valve and the one or more slits of the valve can open due to the activation end of the actuator pushing against the valve disc. The two elongated elements can un-flex and return to their more natural state, which includes moving away from one another, or can remain inwardly deflected if being constrained by the distal shoulder or other surfaces within the catheter hub when the male Luer tip is removed.

An aspect of the present disclosure is understood to include a catheter assembly comprising a valve with a valve body and wherein a valve perimeter of the valve body can seat within a bore section of the catheter hub at a stepped surface. The valve can have a shoulder and can abut a shoulder inside the interior of the catheter hub to limit distal advancement of the valve.

The shoulder of the valve is defined by a distal valve body perimeter having a first diameter and a proximal valve body perimeter having a second diameter, which is larger than the first diameter.

The valve, which can also be called a septum, can have a proximal cavity or proximal receptacle and a distal cavity or distal receptacle with a valve disc located therebetween.

The proximal and distal receptacles of the valve can have different shaped surfaces. The proximal receptacle can have an inverse frusto-conical surface. The distal receptacle can have an inverse dome surface.

A still yet further aspect of the present disclosure is understood to include a valve opener for opening the valve. The valve opener can be configured to push the valve against another structure, such as the bushing, against a stepped surface inside the catheter hub, or both.

The valve opener can have nose section with an activation end and wherein the activation end and at least part of the nose section can be located inside a bore of the valve in a ready to use position, prior to activation. The nose section of the actuator and the bore of the valve can have a size-on-size fit.

In a yet further aspect of the present disclosure, the actuator comprises one or more elongated elements, such as two elongated elements or more than two, extending in the proximal direction relative to the nose section. For example, two elongated elements can extend from the body section of the actuator and each having a fixed end attached to the body section and a free end that is free to independently deflect or move.

Each of the two free ends, one on each of the two elongated elements, can deflect radially inwardly when activated by a male medical implement during activation of the valve. Each of the two elongated elements can also have bumps configured to engage a tip protector or needle guard.

The free ends of the actuator can each comprise a radially extending tab for placement in a groove having a distal shoulder and a proximal shoulder inside an interior of a catheter hub.

The body section of an actuator can have a surface defining a bore having two open ends. The surface can be continuous or can have slots or grooves to define flow channels.

The body section of an actuator can have an outer diameter having a first dimension and the two elongated legs can define and outer diameter having a second dimension and wherein the second dimension is larger than the first dimension.

One or more guiding arms can extend radially from a body section of an actuator. Each guiding arm can seat within a corresponding slot formed inside the interior cavity of the catheter hub. The slot can extend in an axial direction relative to a lengthwise axis of a catheter hub to angularly align the actuator so that the actuator does not rotate.

In a still further aspect of the present disclosure, a catheter assembly is provided comprising a valve, a valve opener, a needle hub with a needle, and a catheter hub with a catheter tube.

The valve assembly can further include a tip protector for blocking the needle tip in a needle protective position.

Following successful venipuncture, a male tip, such as a male Luer, can be inserted into a proximal opening of the catheter hub to advance the valve opener in a distal direction and open the valve. The valve, the valve opener, the needle hub, and optional tip protector can have structural features disclosed elsewhere herein.

A needle guard comprises a proximal wall comprising a perimeter defining an opening. The proximal wall has a proximally facing wall surface and a distally facing wall surface opposing the proximally facing wall surface.

At least one resilient arm extends distally of the proximal wall.

Two resilient arms can extend distally of the proximal wall. One arm can be longer than the other arm. Each arm can also include different arm widths, including a first arm section of a first width and a second arm section of a second width, which is smaller than the first width.

The two arms of the needle guard can originate from different ends of the proximal wall and can cross one another at their respective second arm sections. Thus, when viewed from a side along the lengthwise direction of the needle guard, the two arms intersect one another.

When used with a needle, the two arms of the needle guard intersect one another when in a ready to use position and when in the protective position. In an alternative embodiment, the two arms originate from different ends of the proximal wall and extend in a distal direction without crossing one another. Thus, the two arms can also have essentially the same arm width along the length of each respective arm.

A distal wall is provided at an end of each arm. Optionally only one distal wall is employed. The distal walls can overlap one another along an axial direction of the needle guard by utilizing different arm lengths and/or angling one of the walls at an intersection between the distal wall and the resilient arm.

The intersection of each arm, if two arms are utilized, can engage a corresponding guard engagement section or bumps on the actuator to removably secure the needle guard within the catheter hub in the ready position and during the transition process of removing the needle from the catheter hub.

The ends of the two distal walls can optionally rest on bumps formed on an actuator in a ready to use position without the distal walls or the arms engaging the catheter hub in a ready to use position.

The needle guard may be folded from a stamped metal sheet to form the guard. Ribs may be formed on the arms, the proximal wall, and/or the distal walls to increase structurally rigidity.

An actuator embodiment can have two pairs of bumps formed on opposite plunger elements.

The bumps described herein can be unitarily formed with the plunger element or plunger elements or separately formed and subsequently added to the plunger element or plunger elements. The plunger elements of the actuators can each include an outward protrusion or radial tab with surfaces sized and shaped for contact by a male medical implement.

An actuator embodiment can have a single bump on alternating sides of opposing plunger elements and staggered in the axial direction.

An actuator embodiment can have two bumps on one plunger element, with no bumps on the opposite plunger element. In operation, the arms of the tip protector can engage on only one side with the bumps.

An actuator embodiment can have a single solid bump extending diagonally on each opposing plunger element. The single bump can extend substantially across the plunger element such that single bump can engage both a first arm and a second arm, such as the two ends of the two distal walls, of the tip protector.

An actuator embodiment can have a single solid bump extending diagonally on one plunger element, with no bump on the opposite plunger element.

An actuator embodiment can have extended plunger elements that are better suited for longer length catheter hubs.

The length of any of the actuators described herein can be selected so that when a male Luer tip is inserted into a catheter hub, contact can be made with the actuator by the male Luer tip as the male tip seats against the proximal opening, such as the female Luer of the catheter hub.

The contact with an actuator by a male tip can include a distal travel applied by the male tip on the actuator to advance the actuator against a valve to open the valve.

An actuator embodiment can have extended plunger elements with additional protrusions that increase the surface area of engagement with various Luer tips.

Actuators can also include external bumps formed on an outer surface of each elongated element as well as on the inner surface of each elongated element. The external bumps can be sized and shaped to contact proximal and distal shoulders of a groove inside a catheter hub.

A catheter hub provided herein can have one or more ribs formed on the interior surface of the hub.

An actuator embodiment can have one or more slots and one or more undercuts formed on one or more plunger elements.

Ribs can form on an interior surface of a catheter hub to engage with the slots formed on the actuator to provide an anti-rotation feature that reduces or eliminates rotation of the actuator.

Voids can form on the interior surface of a catheter hub to aid in the seating of a needle protector.

Bumps formed on the interior surface of a catheter hub can engage with undercuts on an actuator to help hold the actuator in place, such as from displacing out the open proximal end of the catheter hub.

An aspect of the present invention further includes a needle assembly comprising: a needle hub with a needle extending from a distal end of the needle hub; a catheter hub having an interior surface defining an interior cavity; a catheter tube attached to the catheter hub and having the needle extending through the catheter tube and having a needle tip extending out a distal opening of the catheter tube in a ready to use position; a valve positioned in the interior cavity of the catheter hub, said valve comprising a valve body having an outer perimeter positioned in a bore section of the catheter hub, a proximal receptacle on a proximal end, a distal receptacle on a distal end, and a valve disc located between the proximal receptacle and distal receptacle; an actuator positioned in the interior cavity of the catheter hub, the actuator is configured to open the valve, the actuator comprising: a body having a nose section and an activation end, the activation end is located within the proximal receptacle and is configured to push the valve disc to open the valve; and an extension leg on a proximal end of the actuator, the extension leg having an engagement section having a surface for supporting; a safety clip having a proximal wall, a proximal opening on the proximal wall, a resilient arm, and an end; wherein the end of the arm is supported by the surface of the engagement section when the safety clip is in the interior cavity of the catheter hub in the ready to use position.

The actuator can further comprise a radially extending tab formed on the extension leg located in an undercut formed on the interior surface of the catheter hub, the location of the radially extending tab in the undercut can prevent dislodgement of the actuator from within the interior cavity of the catheter hub.

The undercut can have a proximal shoulder and a distal shoulder and wherein the radially extending tab can be located closer to the proximal shoulder than the distal shoulder in the ready to use position.

The actuator can comprise one or more guide arms extending radially from the body of the actuator, the one or more guide arms can be configured to engage one or more slots on the interior surface of the catheter hub, the engagement between the one or more guide arms and the one or more slots can prevent rotation of the actuator within the catheter hub.

The actuator can comprise a second extension leg on the proximal end of the actuator spaced from the extension leg, the second extension leg can have a second engagement section for supporting the safety clip.

The actuator can comprise a third engagement section formed on the extension leg near the engagement section and a fourth engagement section formed on the second extension leg near the second engagement section.

The engagement section can be formed opposite the second engagement section and the third engagement section can be formed opposite the fourth engagement section.

The engagement section and the fourth engagement section can be configured to engage with a first arm of a safety clip and the second engagement section and third engagement section can be configured to engage with a second arm of a safety clip, wherein the first arm and second arm of the safety clip can have different lengths.

The extension leg can be a first extension leg and wherein the engagement section is formed on an inner surface of the first extension leg and a second engagement section is formed on an inner surface of a second extension leg, diagonally to the engagement section.

A needle clip can be provided for use with the catheter hub, the needle clip can comprise a proximal wall with an opening and an arm with an end, and wherein the end can be supported by the engagement section and not rest on the needle in the ready to use position.

An aspect of the present invention can include method of manufacturing a needle assembly. The method can comprise: providing a catheter hub with a catheter tube with a distal opening, said catheter hub comprising a hub body defining an interior cavity and a proximal opening; positioning a bushing inside the catheter hub and against the catheter tube and positioning a valve proximal of the bushing; the valve comprising a valve body having a distal valve section and a proximal valve section defining a proximal receptacle, and wherein the distal valve section is located in a bore section of the interior cavity and the bore section contacts the distal valve section to secure the valve inside the interior cavity; positioning a valve opener adjacent the valve and inside the interior cavity of the catheter hub so that a nose section of the valve opener is located inside the proximal receptacle, the valve opener comprising an extension leg on a proximal end of the valve opener, the extension leg having an engagement section; positioning a safety clip in the interior cavity of the catheter hub so that an end of an arm of the safety clip is located over the engagement section, the engagement section having a surface to support the safety clip when the safety clip is in the interior cavity of the catheter hub; placing a needle, which is attached to a needle hub, through the catheter hub, the valve, the valve opener, the safety clip and the catheter tube so that a tip of the needle extends out the distal opening of the catheter tube.

The method can comprise locating a guiding arm extending from the valve opener in a slot form in the interior cavity of the catheter hub to prevent rotation of the valve opener.

The method can comprise providing a radially extending tab on the extension leg spaced from the engagement section; said radially extending tab can have a planar surface.

The method can further comprise a second extension leg comprising a second engagement section and a second radially extending tab, wherein said radially extending tab on the extension leg and said second radially extending tab on the second extension leg can provide surfaces for a male Luer tip to push against to open the valve.

The method wherein the extension leg and the second extension leg can move radially when surfaces of the radially extending tab and second radially extending tab are pushed by a male Luer tip.

BRIEF DESCRIPTION OF THE DRAWINGS

These and other features and advantages of the present device, system, and method will become appreciated as the same becomes better understood with reference to the specification, claims and appended drawings wherein:

FIG. 5B is a schematic cross sectional view of the catheter hub of FIG. 1 showing an embodiment of an anti-rotational slot formed on its interior surface.

DETAILED DESCRIPTION

The detailed description set forth below in connection with the appended drawings is intended as a description of the presently preferred embodiments of catheter assemblies with control valves provided in accordance with aspects of the present devices, systems, and methods and is not intended to represent the only forms in which the present devices, systems, and methods may be constructed or utilized. The description sets forth the features and the steps for constructing and using the embodiments of the present devices, systems, and methods in connection with the illustrated embodiments. It is to be understood, however, that the same or equivalent functions and structures may be accomplished by different embodiments that are also intended to be encompassed within the spirit and scope of the present disclosure. As denoted elsewhere herein, like element numbers are intended to indicate like or similar elements or features.

Figure 1:
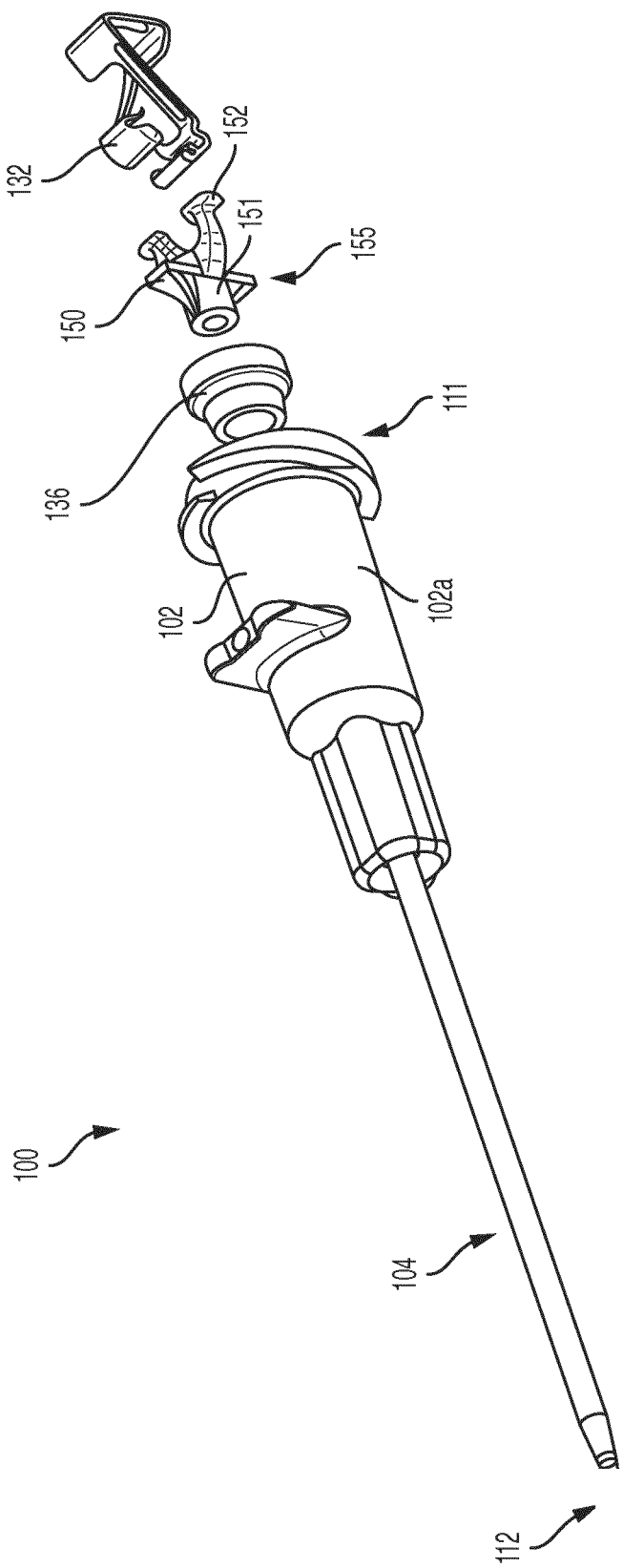
FIG. 1 is an exploded perspective top view of an embodiment of a catheter assembly.

FIG. 1 is an exploded perspective top view of one embodiment of a catheter assembly 100. As shown in FIG. 1, the catheter assembly 100, which may more broadly be referred to as a needle assembly or a needle device, is shown comprising a catheter hub 102 with a catheter tube 104 attached to the catheter hub. Interiorly of the catheter hub 102, a septum or valve 136, an actuator 150 and a safety clip 132, such as a needle guard or tip protector, are provided. A needle and needle hub (not shown) can be inserted through the proximal opening 111 of the catheter hub 102, through the catheter tube with the needle tip protruding from the distal opening 112 of the catheter tube.

The tip protector 132 is configured to be removed with the needle and needle hub following use, such as following successful venipuncture, and the valve 136 and valve actuator 150 remaining inside the interior of the catheter hub for controlling fluid flow therethrough. The actuator 150 is configured to be pushed into the valve 136 to open the valve for fluid flow. In an example, a male Luer tip can be inserted into the proximal opening of the catheter hub after removal of the needle to then push the actuator 150 distally into the valve to open the valve.

In some embodiments, the actuator 150 comprises a body 151, one or more extension legs 152, and one or more guiding arms or guide arms 155. The body 151 can be rigid or semi rigid. The body can be configured to engage with the valve 136 to open the valve as an axial force is applied to the actuator towards the distal end of the catheter assembly 100, such as during the insertion of a male Luer. Generally, the body is rigid relative to the more pliable valve 136, which allows the body, such as the nose section of the actuator with the activation end, to actuate the valve, such as to deflect at least part of the valve to open the valve for fluid communication between a region distal of the valve and a region proximal of the valve. For example, the body of the actuator can be made of a non-compressible material, such as metal, or a somewhat compressible material such as a hard elastomer. A rigid plastic material may also be used to form the actuator 150, such as a polycarbonate material. The nose section of the body can be elongated and can have a passage or bore passing through the nose section. The bore at the nose section can provide a pathway for fluid flow and can accommodate a needle in a ready to use position of the catheter assembly.

The extension legs 152 present a structure for a male Luer tip to push against. The extension legs 152 may have one or more bumps or engagement sections 330 (FIGS. 2A-3C) on each leg for engaging one or more arms of the safety clip 132, which can prevent dislodgement of the safety clip from the interior cavity of the catheter hub while in the ready to use position. For example, two end surfaces of the safety clip 132 can engage or can rest against the one or more bumps 330 on the extension legs in a ready to use position instead of pressing against a side of the needle and against the interior of the catheter hub. While embodiments of the engagement sections comprise bumps, other embodiments can comprise undercuts, notches, protrusions, ridges or other features that can engage with or can support an arm or arms of the safety clip. In one embodiment, the one or more guiding arms 155 can extend radially from the body 151 to engage an anti-rotation feature on the catheter hub, such as a slot formed axially on the interior surface of the catheter hub, which prevents rotation of the actuator. The extension legs 152 can extend axially from the body 151. A gap can be provided between the two extension legs 152. A flange can be located at an end of each extension leg 152 to provide abutting surfaces for a male Luer tip, as further discussed below.

Figure 2:
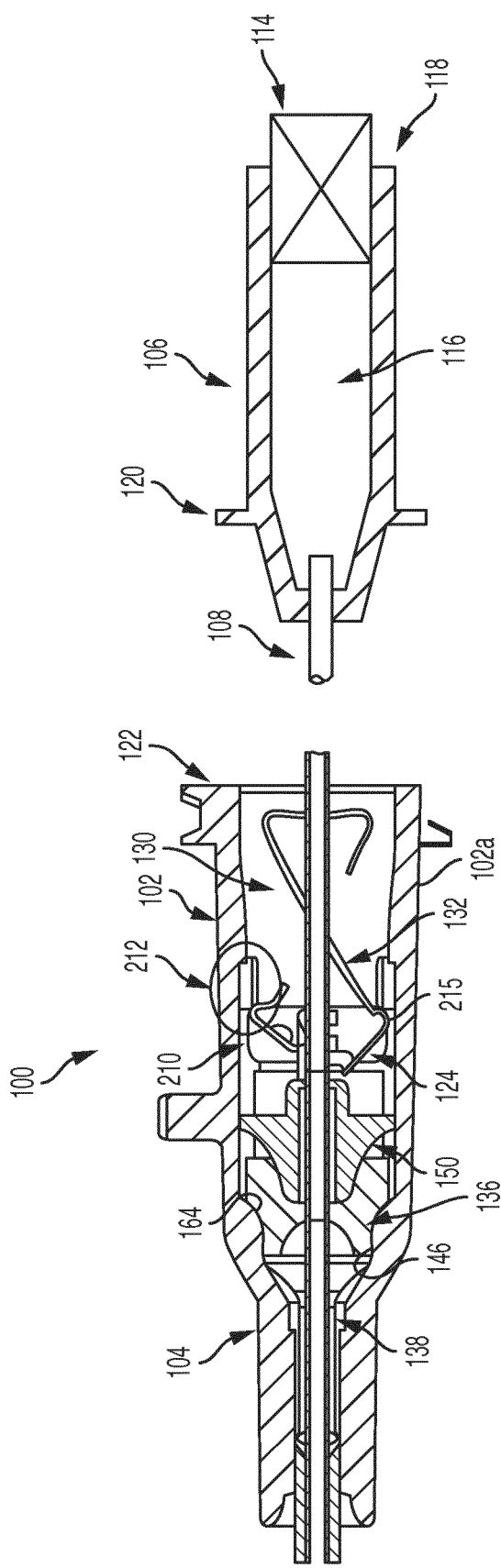
FIG. 2 is a schematic cross-sectional side view of the catheter assembly embodiment of FIG. 1 in a partially withdrawn position in which the needle is still located inside a catheter tube.

FIG. 2 is a schematic cross-sectional side view of a catheter assembly embodiment 100 in a partially withdrawn position in which the needle 108 is retracted in the proximal direction relative to the catheter hub 102 but not completely or fully withdrawn away from the catheter hub. Thus, the needle hub 106 is shown in a partially withdrawn position with the needle 108 extending through the catheter hub 102 and through the catheter tube 104.

In a ready position with the needle hub 106 in contact with the catheter hub 102 and the needle tip 110 extends out the distal end or distal opening 112 of the catheter tube 104, the catheter assembly 100 is ready for use, such as to perform a venipuncture or intravenous access. Sometimes the ready position first requires removing a protective cap (not shown) from the catheter assembly or needle assembly 100 to expose the needle tip.

A flash back plug 114 can be provided at the proximal end 118 of the needle hub 106, which is removable from the needle hub and allows air to vent into the flash back chamber 116 but stops blood from spilling out the proximal end 118 when entering the flashback chamber 116 during primary flashback. Alternatively, a syringe can be attached to the proximal end of the needle hub. Instances of the valve and actuator described further below can also be placed within the needle hub as a second valve. The needle hub 106 can further comprise a shoulder 120, tab, or other surfaces that physically contact the catheter hub 102, such as the proximal end surface 122 of the catheter hub, to axially register the two hubs 102, 106 to set the length of the needle tip 110 projecting out of the distal opening 112 of the catheter tube 104.

Interiorly of the catheter hub 102, in the interior cavity 130, the safety clip 132, also called a needle protective element, needle guard, or tip protector, the valve opener or actuator 150, the septum or valve 136, and a bushing 138 are provided. The proximal opening of the catheter hub 102 can be sized with a female Luer taper to receive a male Luer tip. The bushing 138 is configured to wedge the proximal end of the catheter tube 104 against the interior wall surfaces of the catheter hub 102 to retain the catheter tube 104 to the catheter hub 102, which is conventional.

The safety clip, needle guard, or tip protector 132 may embody any number of prior art guards configured for blocking the needle tip 110 of the needle. In the exemplary embodiment shown, the tip protector 132 can embody one of the guards shown in U.S. Pat. No. 6,616,630, the contents of which are expressly incorporated herein by reference. For example, the tip protector 132 can have a proximal wall and two resilient arms each with a distal wall and wherein a change in profile 144 (FIG. 5A) on the needle 108, such as a crimp or a bulge, engages a perimeter defining an opening on the proximal wall of the tip protector 132 to retract the tip protector in the proximal direction out of the catheter hub following successful venipuncture.

The two arms can intersect as described in U.S. Pat. No. 6,616,630 and shown in FIG. 7 or they can run along different sides of the needle and do not intersect along a side view. In one embodiment, the needle guard arms are spread by the actuator 150 in a ready position, such as by the bumps or engagement sections 330, and not by the needle shaft and the spreading of the arms forces the arms of the needle guard to engage the inside of the catheter hub, such as the guard engagement section 210 (e.g., an undercut or groove) of the catheter hub 102. In some example, the arms are spread by the actuator but the arms do not engage the interior of the catheter hub in the ready to use position. For example, the radial outermost surfaces 215 of the arms, such as the elbows between the elongated part of the arms and the distal walls, do not engage or contact the interior of the catheter hub since the arms do not rest on the needle but rather rest on the bumps and the needle guard is therefore retained inside the interior of the catheter hub by the engagement with the bumps on the actuator. For example, a gap can be provided between each outermost surfaces 215, such as the elbows, and the interior of the catheter hub when the arms engage the bumps of the actuator.

Thus, during retraction of the needle following use, the needle guard can be retained inside the catheter hub by the engagement between the arms on the needle guard and the bumps on the actuator. As the needle is withdrawn following use and a crimp on the needle engages the proximal wall of the tip protector, such as engage the proximal defining the opening on the proximal wall, the elbow 215 of an arm of the tip protector 132, if one arm, or two elbows on two arms of the tip protector, can deflect outwardly into the space provided by the gaps between the elbows and the interior wall surfaces of the catheter hub or can flatten out if in contact with the catheter hub, such as against an edge 212 of the guard engagement section 210 of the catheter hub and against the valve actuator, causing the arms to move and release from the bump(s) on the extension leg(s) of the actuator.

When the needle tip 110 is pulled into the needle guard 132 following successful venipuncture, such as when the needle tip moves proximally of the distal wall or the two distal walls, the arms of the needle guard collapse to their protecting position after the distal walls of the arms move proximally of the corresponding bumps on the actuator to which the arms rest to block accidental access to the needle tip. In one example, one or two distal walls at the ends of the arms move distal of the needle tip to block the needle tip from accidental needle sticks. After the engagement of the arms with the bumps on the actuator plunger elements is released, the tip protector can be removed from the catheter hub in the proximal direction along with the needle. The same working can also be achieved by one of the one arm needle guards described in U.S. Pat. No. 6,616,630, which runs along a side the needle shaft, instead of crossing the needle as view from a side of the needle and as shown in some of the embodiments of the '630 patent. Likewise, the distal wall of the one arm is pushed aside by the needle shaft in the ready position. When the needle tip 110 is moved proximal of the distal wall, then the distal wall springs in front of the needle tip to block accidental access to the needle tip and at the same time the engagement between the needle guard and bumps is released. Usable needle guards can be unitarily formed, such as by injection molding or by cold working a stamped metal sheet, or be assembled together using two or more separately formed sub-components.

Figure 3C:
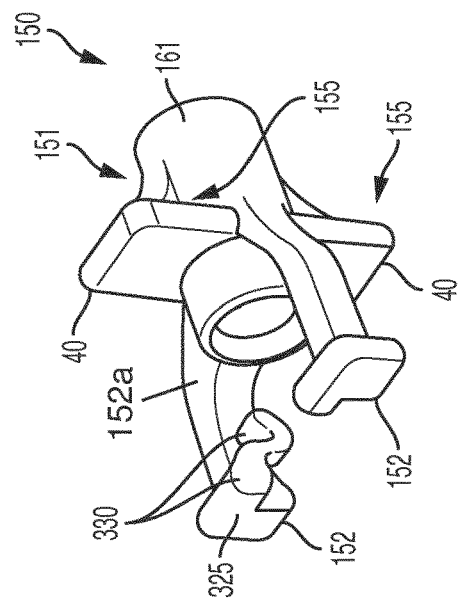
FIGS. 3A-3C illustrate front view, top view, and rear perspective view of the valve opener or actuator embodiment of FIG. 1.
Figure 3B:
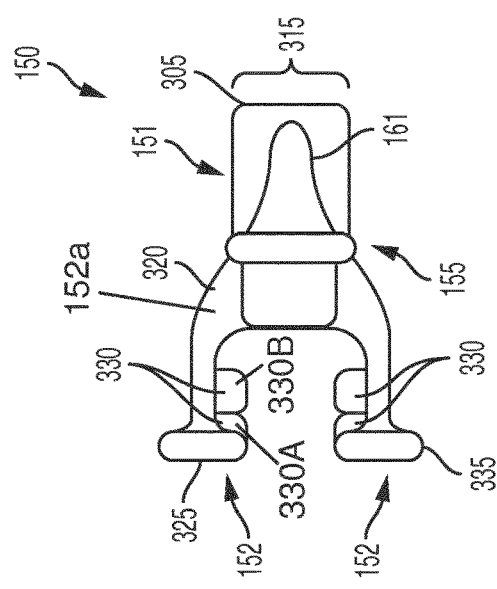
Figure 3A:
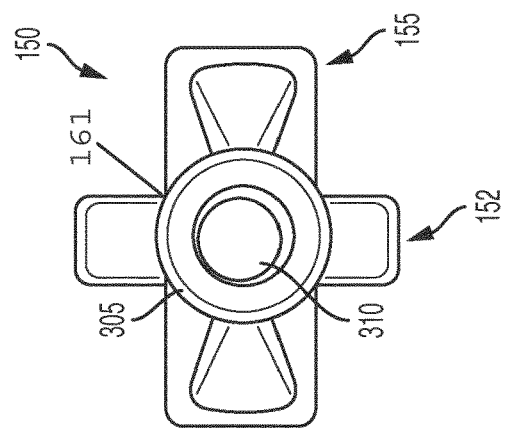

FIG. 3A shows a front view of an embodiment of the valve opener or actuator 150 of FIG. 1, looking down the nose section of the actuator. FIG. 3B shows a top view of the same valve opener and FIG. 3C shows a rear perspective view of the valve opener 150. With further reference to FIG. 1 and FIGS. 3A-3C, the valve opener 150 can comprise a body 151 with a nose section 161, one or more extension legs or plunger elements 152 (e.g., such as a leg element or elongated extension), and one or more guiding arms 155. In an example, the actuator or opener 150 has a lengthwise axis, the one or more guiding arms 155 extend radially relative to the lengthwise axis and the one or more extension legs 152 extend axially along the lengthwise axis. The extension legs 152 can have linear or straight leg portions or can have curved portions extending from the body and then linear portions or straight portions along the axial direction. The two linear portions can have a gap therebetween.

In a particular example, two guiding arms or guide arms 155 are diametrically opposed to one another along the lengthwise axis. The guiding arms 155 can each embody a rectangular or square structure having a generally straight or flat outer most edge 40, which can optionally be curved, undulating, serrated, or arc-shape. The rigid body 151 can have an elongated shape, such as a cylindrical shape, forming an activation end 315 that can embody a ring or annular shaped structure at the distal end. The elongated body can optionally have a draft angle or an inward taper in the distal direction.

In operation, the activation end 315 can press into the valve 136 of FIG. 1, when pushed distally by a male medical implement, such as a syringe tip, a Luer adapter, or an IV line, to actuate the valve. In the ready position, the activation end 315 may be in contact with the valve 136 but may optionally be spaced from the proximal surface of the valve disc. As shown in FIG. 2, the activation end 315 can be fitted into a receiving space of the valve, such as a cavity on a proximal side of the valve, and in contact with the valve, such as in contact with the surface defining the bore of the receiving space and/or the surface of the valve disc, as further discussed below. In some examples, the activation end 315 of the actuator can have a groove or a catch section to engage the valve for use as a one-time opening of the valve without re-use. With the groove or catch section on the actuator, the valve, such as the flaps of the valve defined by the one or more slits, can engage the groove or catch section so that actuator can remain engaged to the valve after removal of the male Luer tip.

In an exemplary embodiment, two plunger elements 152 can extend from the rigid body 151 of the actuator in the proximal direction and each can have a length measured in a lengthwise direction of the catheter assembly and a width, measured orthogonally to the length. Other embodiments may use one or three or more leg extensions or plunger elements 152 extending from the rigid body 151. Each plunger element or leg extension can have a round cross section or a multi-sided cross-section, such as a polygonal shaped cross-section. The cross-section can optionally have an irregular shape.

In an embodiment, each plunger element 152 is sized and shaped for contact by a male Luer to then transfer a distally directed force from the male Luer, through the nose section, to the activation end 150 to then push against the valve 136 to separate the one or more slits on the valve, as further discussed below. In an example, the leg extensions or plunger elements are flexible and deflectable so that when pushed by a male Luer tip, the plunger elements deflect or flex. The plunger elements are deflectable by selecting a material that has the requisite resilient properties. In other examples, the plunger elements are deflectable by incorporating one or more weakened sections, such as by incorporating a structurally thin section, by incorporating cut-outs, by incorporating kinks, by employing a small cross-section compared to other sections of the same elongated plunger element, or combinations thereof. Alternatively, the plunger elements can be flexible and deflectable by selecting a material that has the requisite resilient properties and by incorporating one or more weakened sections.

As can be visualized from the FIGS. 3B and 3C, the plunger elements 152 can each have an arc shape or arc cross section 152a along a width of the actuator, similar to a crescent moon. In another example, each plunger element 152 can be generally flat or planar along a cross section. In still other examples, each plunger element has more than one different cross-sectional profiles or contours along a length section. For example, an elongated plunger element can have a square profile located adjacent a crescent-shaped profile. In an embodiment, the thickness of each of two plunger elements 152 is sufficiently small or thin so that the needle guard 132 and the two plunger elements 152 have sufficient clearance to fit within the interior cross-sectional space of the catheter hub 102 without being physically binding against the catheter hub and rendered unmovable or fixed. In an example, the thickness of each of two plunger elements 152 and the width of the needle guard are such that no undercut or channel is required to be formed in the interior wall surfaces of the catheter hub 102 to accommodate them. When the plunger element 152 has an arc cross section, it can be mechanically stronger to take a greater load when being pushed by a male tip to push the activation end 150 against the valve 136. This allows a thin and compact design for the infusion device and gives more room in the standardized space of a female Luer taper.

The valve opener 150 can be made from a metal material or from a plastic material or from both. When made from a metal material, the valve opener 150 can be formed by deep draw methods and the arc shape cross section of the plunger element 152 can provide added rigidity when pushed by the male Luer. Each plunger element 152 can comprise at least two lengthwise edges and a rib can be provided along one or both of the lengthwise edges to further add structural rigidity. One or more welds may be used to facilitate with the assembly of a metal actuator. One or more gaps 154 can be provided between any two plunger elements 152. The gaps 154 can provide clearance or space for fluid flow flowing thereacross, such as during IV infusion. The gap 154 can also be utilized to accommodate a needle guard 132, as shown in FIG. 1, and to accommodate a needle in a ready to use position.

The rigid body 151 of the valve opener 150 can comprise an exterior surface defining an outer perimeter 305 and an interior surface defining a cavity or a bore. In an example, the outer perimeter 305 is generally cylindrical. In other examples, the outer perimeter can have a taper and can optionally include surface features such as bumps or grooves. Interiorly, the body 151 comprises a bore 310 and openings at each end of the bore. The body 151 can have a continuous surface with no gaps or slots or with gaps/slots to facilitate fluid flow.

The distal edge or intersection of the activation end 315 and the outer perimeter 305 can have a sharp edge or a blunt edge, such as a chamfer. In an example, the activation end is a blunt edge comprising a planar surface for pushing against the valve 136, as further discussed below. On the proximal side of the rigid body 151, the two plunger elements 152 can extend outwards from the outer perimeter 305 to form a shoulder 320. Said differently, the outer perimeter 305 can have an outside diameter of a first dimension and the two plunger elements 152 can define an outside profile of a second dimension, which is larger than the first dimension. A shoulder 320 is provided between the two different dimensions.

Figure 3D:
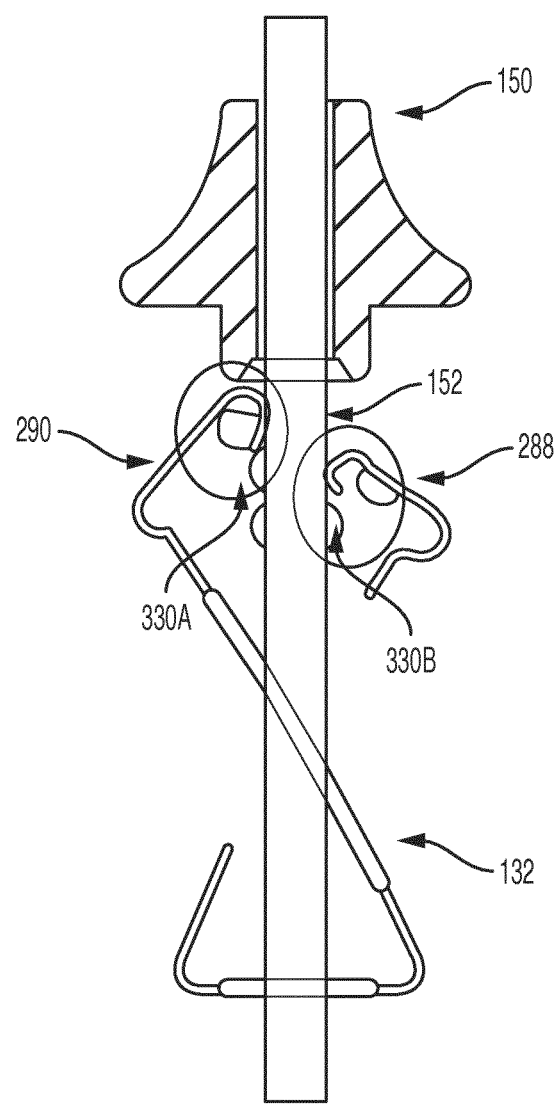
FIG. 3D illustrates a cross-sectional view of a tip protector embodiment of FIG. 1 engaging with the actuator embodiment of FIG. 1.

As illustrated in FIGS. 3B-3D, one or more bumps 330, or engagement sections or segments, may be formed on the leg extension or plunger elements 152. In some examples, one or more bumps or engagement sections 330 can be formed on each leg extension, such as on the inside surface of each leg, at the gap between the two leg extensions. The bumps can be sized and shaped to engage with one or more arms of the safety clip or tip protector 132 (not shown), which can prevent dislodgement of the tip protector from the interior cavity of the catheter hub while in the ready to use position. The bumps or engagement sections can also be provided to support the arms of the needle guard so that the arms are spaced from the needle in the ready to use position. The one or more bumps 330 can serve as mounting surfaces for the ends of the two arms of the tip protector 132, such as for the ends of distal walls of the arms, to rest thereon instead of against the needle shaft. This can help to decrease drag between the needle guard and the needle during retraction of the needle following successful venipuncture as there is no contact between the needle shaft and the ends of the two arms when the ends are rested on the bumps. When rested on the bumps, or engagement sections or segments, the needle guard can also contact the interior of the catheter hub or be spaced from the interior of the catheter hub.

In the illustrated embodiment, there are two pairs of bumps 330 opposite each other on the two opposite plunger elements 152. Each pair of bumps on each plunger element can be at a different distance from the proximal ends of the plunger elements 152, with one bump of the pair closer to the proximal edge and one bump of the pair farther from the proximal edge. The different distances can allow each pair of bumps to engage different length arms of the tip protector 132, which are staggered in the axial direction. For example, if each pair of bumps can have a first bump and a second bump, the first bump 330A on each of the two leg extensions can support one arm of the needle guard and the second bump 330B on each of the two leg extensions can support the second arm of the needle guard, where the two arms have different lengths.

The two bumps 330A, 330B on each plunger element 152 can be diagonally formed, such as on different planes, on the interior surface of each plunger element to allow a top arm of the tip protector to engage with a top bump and a bottom arm of the tip protector to engage with a bottom bump, as shown in FIG. 3D.

FIG. 3D illustrates a cross-sectional view of the tip protector 132 and the actuator 150 showing a long arm 290 engaging with a first set of bumps 330A (only one shown) and a short arm 288 of the tip protector engaging with a second set of bumps 330B (only one shown), where the first set of bumps and second set of bumps are at different distance axially along the plunger element 152. In some examples, only one first bump 330A and one second bump 330B are used to support the ends 333 (FIG. 7) of the tip protector. The two single first and second bumps can be located separately on the two leg extensions, one on each leg extension, so that one bump is on one of the leg extensions and another bump is on the other leg extension.

In an embodiment, the proximal end of a plunger element 152 can include an outward protrusion 335. The outward protrusion 335 can engage with an undercut or groove formed on the interior surface of the catheter hub 102 (FIG. 1) to help maintain the position of the actuator 152 within the hub cavity, as further discussed below with reference to FIGS. 5A and 5B. Two outward protrusions 335 on the two plunger elements 152 can have planar surfaces 325 that are orthogonal to the lengthwise axis of the actuator. Said differently, the outward protrusions 335 can embody tabs that have surfaces 325 that extend radially of the plunger elements.

Each of the two outward protrusions or radially extending tabs 335 can provide a physical barrier for a male medical implement to push against to advance the actuator 150 against the valve to open the valve. For example, the distal end of a male Luer tip can push against the surfaces 325 of the tabs 335 to distally advance the actuator. In other examples, the outward protrusions 335 can be omitted where the cross section of the plunger elements 152, without the tabs 335, are sufficiently large to be contacted by the male medical implement. When incorporated, each outward protrusion 335 has a cross-section that is larger than the cross-section of the corresponding plunger element. In other examples, each outward protrusion can have a smaller cross section than the cross section of the plunger element but is strategically placed at the proximal end of the plunger element so as to be contacted by the male medical implement during activation. Optionally, only one outward protrusion 335 is incorporated on one of the two plunger elements 152 to both serve to angularly align the actuator to the interior surface of the catheter hub and to take the load of the male medical implement.

In still other examples, the outward protrusions 335 on the two plunger elements 152 are configured to move in a groove inside the catheter hub between a proximal shoulder and a distal shoulder of the groove. The groove may be viewed as an undercut formed in or on the interior surface of the catheter hub forming a proximal shoulder and a distal shoulder. In the ready to use position of the catheter assembly, the outward protrusions or radially extending tabs 335 on the actuator can abut the proximal shoulder of the groove while the nose section of the actuator 150 can contact the valve to maintain a positive engagement between the actuator and the valve without opening the one or more slits on the valve, as shown and discussed below with reference to FIG. 5A.

In an activation position in which the actuator is advanced distally within the bore of the catheter hub by a male medical implement, the outward protrusions 335 can contact the distal shoulder of the two grooves, if two spaced apart grooves or a single continuous annular groove, inside the catheter hub to delimit the distal travel of the outward protrusions 335 within the grooves. When contacted with the distal shoulders of the grooves, the two plunger elements 152 can be deflected inwardly due to the abutment or contact to assist with flexing the two plunger elements 152, as further discussed below. In an example, when the two plunger elements are flexed during activation, they move closer together. When the male Luer tip is retracted away from the plunger elements 152, the two plunger elements can move further away from one another. Flexing of the plunger elements 152 can move the outward protrusions away from the surfaces of the groove to minimize drag or friction as the actuator is advanced in the distal direction.

Thus, the present valve opener 150 is understood to include abutting proximal surface or surfaces 325 on the outward protrusions or radial tabs 335 of the two plunger elements 152 that are sized and shaped to be pushed against by a male Luer tip or a syringe tip when said tip is inserted into the proximal opening of the catheter hub 102 following successful venipuncture to push the valve opener 150 distally to open the valve 136. The outward protrusions 335 having the abutting surfaces 325 may be referred to as radially extending tabs. One or more radially extending tabs can extend from each plunger element. As the two plunger elements 152 are pushed distally, they can flex or deflect. In an example, the two plunger elements 152 are deflected when pushed distally by a Luer tip and move closer to one another. The deflection of the two plunger elements can then space the two radial tabs from the interior surfaces of the catheter hub to then reduce drag or friction as the actuator is advanced in the distal direction by the male Luer tip.

Figure 4A:
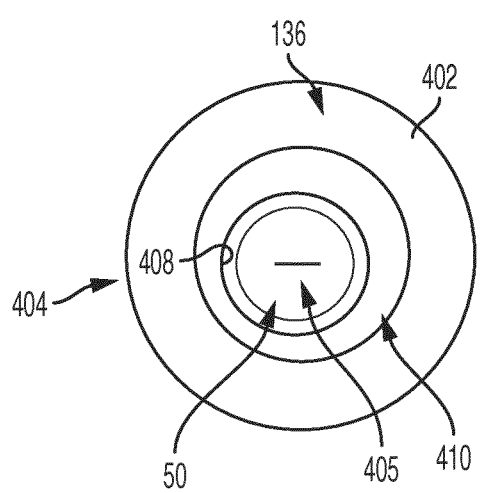
FIGS. 4A-4D illustrates a proximal view, a distal view, and a cross-sectional view of the valve embodiment of FIG. 1.
Figure 4B:
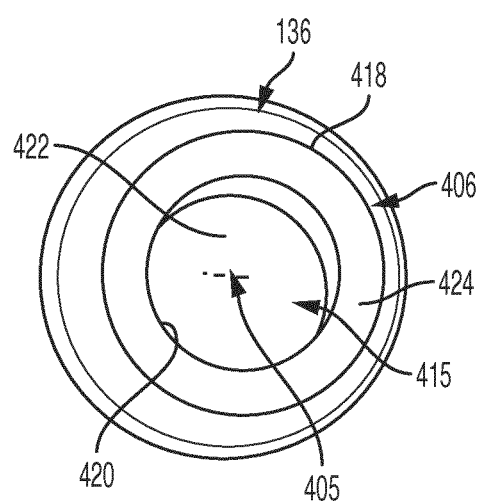
Figure 4C:
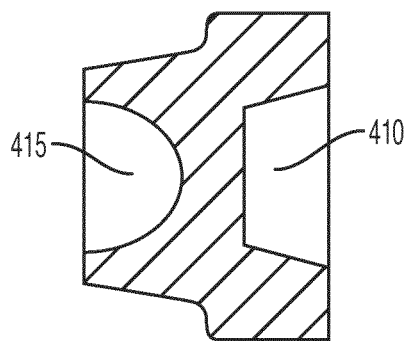
Figure 4D:
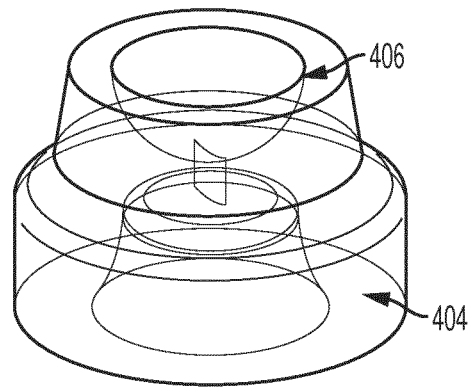

FIG. 4A illustrates a proximal view of the valve 136 of FIG. 1, looking at the proximal surfaces of the valve. FIG. 4B illustrates a distal view of the same valve 136, looking at the distal surfaces of the valve. FIG. 4C illustrates a cross-sectional view of the same valve 136. FIG. 4D illustrates a side perspective view of the valve 136. With reference again to FIG. 2 and FIG. 3C, when installed, the valve 136 is located inside the catheter hub 102 just distal of the groove 124 having proximal and distal shoulders and just proximal to the bushing 138 that secures the catheter tube to the catheter hub. In some examples, the valve 136 can touch the bushing 138. In other examples, the valve 136 can be spaced from the bushing. An internal shoulder can be provided inside the interior cavity of the catheter hub to support the valve from distal displacement.

In an example, the valve 136 comprises a valve body 402 comprising a body diameter sized to seat within the catheter hub, and a valve disc 50 having thickness measured orthogonal to the body diameter, and one or more slits 405 defining two or more flaps formed through the thickness of the valve disc. For example, one or two or three slits 405 may be provided through the valve thickness to define two to three flaps. In the illustrated embodiment, one slit 405 extends through the center of the valve disc. In other examples, there can be more than three slits and more than three flaps.

With reference to FIGS. 4A and 4D, the valve 136 is shown with a proximal valve section 404 and a distal valve section 406. The proximal valve section 404 is provided with bore 408 having a frusto-conical surface 410. The frusto-conical surface 410 can be configured to engage with the activation end 315 and part of the nose section 161 of the rigid body 151 of the actuator 150 in a ready to use position. In some embodiments, the surface of the bore 408 of the valve may be formed into other shapes and still function as a receptacle for the activator, such as an inverse cylinder or inverse rectangular or cubic box. The distal end of the bore 408 can be bounded or blocked by the valve disc 50, which has one slit 405 with two or more slits defining two or more flaps contemplated.

FIG. 4B shows the distal valve section 406 having an exterior surface 418 and an interior surface 420 defining a bore 422. A distal end edge 424 is provided between the interior and exterior surfaces. As shown, the bore 422 comprises an inverse dome surface 415, such as a concave surface, formed on the distal side of the valve 136. The dome surface 415 can provide space for the valve 136 to collapse when a Luer tip is inserted into the catheter hub 102. This can allow the valve and the actuator to remain engaged even after removal of the male medical implement used to advance the actuator into the valve, as further discussed below.

The valve 136 therefore can comprise a distal cavity or distal receptacle 415 and a proximal cavity or proximal receptacle 410. The distal cavity 415, otherwise called a distal receptacle, can have a dome shape or surface. The proximal cavity 410, otherwise called a proximal receptacle, can have an inverse frusto-conical surface. The valve disc 50 can comprise one or more slits 405 defining two or more flaps and can be located between the proximal and distal cavities 410, 415. The proximal cavity 410 can accommodate a nose section of an actuator and the distal cavity 415 can accommodate expansion of the two or more flaps of the valve disc 50 when the valve disc is pushed distally by the nose section of the actuator.

In another embodiment, three slits can originate from a point and extend radially from about a center point or central portion of the valve disc 50, similar to a three-point star, to form three flaps that can deflect along the slits.

The valve 136 can comprise an outer perimeter that can float inside the interior cavity of the catheter hub, between the valve opener 150 and the bushing 138. For example, the outer perimeter of the valve 136 can move proximally and distally within the interior cavity 130 of the catheter hub 102 and not be restrained by the catheter hub, such as a shoulder inside the catheter hub, along an axial direction of the catheter assembly. In an embodiment, at least some part or all of the distal edge or intersection of the activation end 315 of the actuator is recessed from the outer perimeter of the valve 136 so that the distal edge can abut or touch the proximally facing wall surface of the valve disc to open the valve disc 50, as further discussed below.

In a particular example, as shown in FIG. 2, the distal valve section 406 is inserted into a bore section 146 of the catheter hub 102, at the distal end of the interior cavity 130. The distal valve section 406 can be press fit into the bore section 146 and the blunt distal end 424 contact the bushing 138. The intersection between the proximal and distal valve sections of the valve 136 as well as the proximal and distal valve sections can seat against a corresponding shoulder or stepped surface 164 formed in the interior cavity 130 of the catheter hub 102 to axially fix the valve within the catheter hub, and not allow the valve to axially move within the interior of the catheter hub. In some examples, the distal end 424 of the valve can be spaced from the bushing.

The valve 136 can be positioned inside a single hub body 102a of a catheter hub 102, such as by advancing the valve against an interior shoulder within the interior cavity of the catheter hub 102, as discussed above. In other words, the valve 136 does not have to be retained inside a catheter hub by two or more catheter hub bodies, such as along a seam of the two or more hub bodies. However, the various components described herein may readily be used with a multi-piece catheter hub without deviating from the scope of the present disclosure. As shown, the outer perimeter of the valve 136 is larger than the interior diameter of the catheter hub so that the valve 136 can be retained inside the catheter hub via a press fit.

Figure 5A:
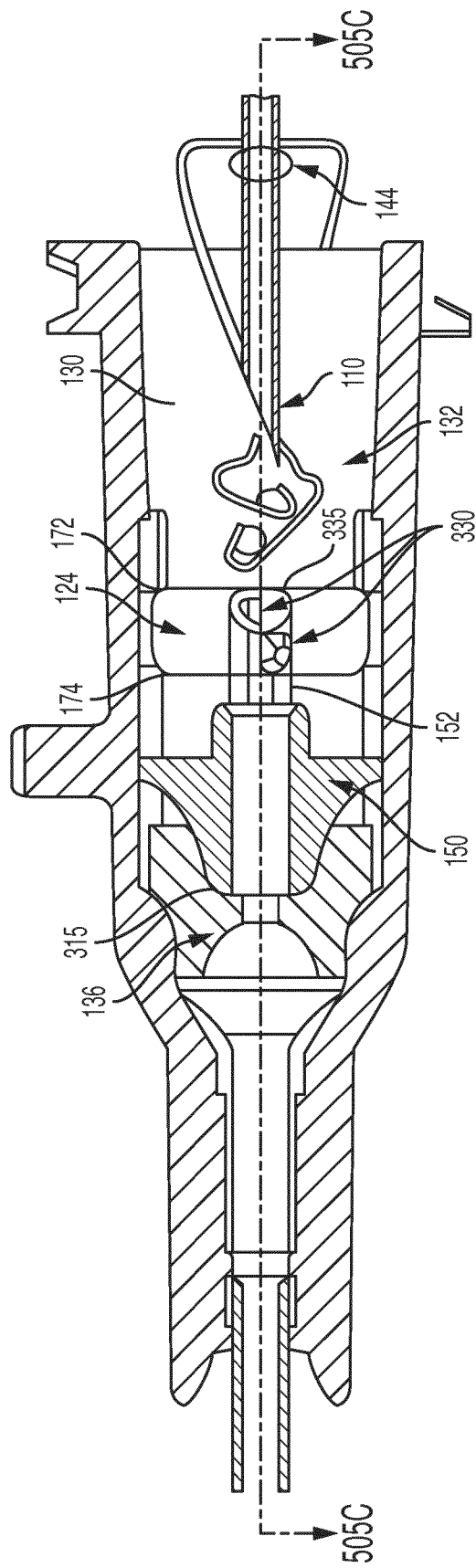
FIG. 5A is a schematic cross-sectional side view of the catheter assembly of FIG. 1 in a transition position or state in which the needle is in the process of being removed from the catheter tube and the catheter hub, such as following successful venipuncture.

FIG. 5A illustrates a similar view to FIG. 2, but further along the needle retraction process with the needle 108 almost completely removed from the catheter hub 102 and the tip protector 132 covering the needle tip 110 in a protective position. With continued reference to FIG. 5A in addition to FIGS. 3A-3C and 4A-4C, the interior cavity 130 has a groove 124, which has a proximal shoulder 172 and a distal shoulder 174. The groove 124 can be annular and two outward protrusions or radial tabs on the two leg extensions can be located in the single annular groove. The groove 124 may be formed as an undercut in the interior surface of the catheter hub.

In the position shown in FIG. 5A but prior to activation, the outward protrusions 335 on the two plunger elements 152 contact the proximal shoulder 172 to limit proximal movement of the actuator or activator 150. In some examples, the outward protrusions 335 can be spaced from the proximal shoulder 172. At the distal end of the activator or actuator, the activation end 315 and the nose section 161 of the rigid body 151 project into the bore 408 of the proximal valve section 404 and the actuator 150 is stopped from moving in the distal direction by the contact with the valve 136. In an example, the contour of the nose section 161, at least at the distal end of the actuator 150, and the bore 408 are the same or are substantially the same, such as having a frusto-conical shape and an inverse frusto-conical shape, to provide a size-on-size fit. In other examples, the nose section 161 and the bore 408 can have dissimilar contours provided at least some parts of the two structures can contact in the ready to use position prior to activation.

In an example, the nose section 161 and the activation end 315 are located inside the bore 408 in a size-on-size fit. In another example, the distal part of the rigid body 151, such as the nose section, is slightly larger than the bore 408 so that the rigid body 151 pre-loads the interior of the bore 408 of the valve in the ready to use position. However, the loading, size, and shape of the various components, such as the valve, the actuator, and the groove, can be selected so that the actuator does not open the one or more slits of the valve disc prior to activation. In other words, once the needle is retracted as shown and the actuator is not activated by a male Luer tip, the valve is closed and no fluid, or at least no significant flow of fluid, passes between the region proximal of the valve and the region distal of the valve, or vice-versa. Further, the contact relationships between the actuator 150 and the groove 124 and between the actuator 150 and the valve 136 limit potential proximal movement of the valve, either during retraction of the needle or following complete removal of the needle from the catheter hub.

In transitioning from the position of FIG. 2 to the position of FIG. 5A, the needle tip 110 moves proximally of two distal walls 300, 302 (FIG. 7), one on each end of the resilient arms 288, 290 (FIG. 7), of the tip protector 132. Alternatively, the needle guard 132 can have one distal wall and/or one arm. As the two distal walls and hence the two resilient arms are pulled proximally by the needle, such as by the change in profile or crimp on the needle pulling on the perimeter defining the opening on the proximal wall of the needle guard, the two arms 288, 290 move radially outwardly to disengage from the two guard engagement sections or bumps 330 of the valve opener 150. Alternatively, the one arm and one distal wall disengage from the one guard engagement section 330. In some examples, the bumps can be provided with inclined surfaces or ramps to facilitate radial outward movement of the two arms as the crimp on the needle pulls on the proximal wall of the needle guard in the proximal direction.

As the needle continues to move in the proximal direction and the change in profile 144 on the needle pulls on the perimeter 282 (FIG. 7) on the proximal wall of the tip protector 132, the tip protector 132 moves proximally with the needle and then upon separating from the bumps 330, the two distal walls on the tip protector close over the needle tip to the position shown in FIG. 5A. Once the covered needle tip is completely removed from the catheter hub, the catheter hub is ready to receive a male medical implement for liquid infusion or for sampling. Prior to insertion of the male medical implement for liquid infusion or for sampling, the valve closes to prevent excessive leakage across the valve.

Alternatively, the needle guard can clamp onto the needle shaft without a crimp and be removed from the catheter hub as a unit. For example, a needle guard with two wall surfaces each with an opening can be used with a needle without a crimp such that when the needle guard is activated, the wall surfaces of the needle guard cant over so that the openings on the two walls clamp against the exterior of the needle shaft.

Note that in the protective position in which the tip protector 132 covers the needle tip 110, the valve 136 remains inside the interior cavity of the catheter hub 102. Thus, the valve 136 is located inside the catheter hub 102 in both the ready position of the needle and the protective position of the needle. Viewed from another perspective, the valve 136 is located inside the catheter hub 102 in both the ready to use position of the catheter assembly 100, in which the needle tip projects out a distal opening 112 (FIG. 1) of the catheter tube 104, and a protective position of the catheter assembly, in which the needle is removed from the catheter hub and the needle tip is covered by a tip protector and the open proximal end of the catheter hub is exposed for infusion or for sampling.

FIG. 5B illustrates a cross-sectional view of the catheter hub 102 taken along line 505C-505C of FIG. 5A. One or more slots 510 can be formed on the interior surface of the catheter hub 102. In the illustrated embodiment, the one or more slots are formed axially along the interior and configured to engage with one or more guiding arms 155 of the actuator 150 of FIG. 1. Thus, there can be two diametrically opposed slots 510 formed in the interior cavity of the catheter hub to receive the two guiding arms 155 on the actuator and to guide the guiding arms as the actuator is advanced by a male Luer tip.

When engaged by a male Luer tip, the actuator can slide in the axial direction but is otherwise restricted from rotating. In an embodiment, two slots 510 are formed on opposite interior surfaces of the catheter hub 102 and are configured to engage two opposite guiding arms or guide arms 155 of the actuator. Other embodiments may use one, three, or more pairs of engaged slots and arms to prevent rotation of the actuator within the catheter hub 102. This can ensure that the actuator 155 moves axially in the correct orientation to actuate the valve 136 of FIG. 1 when a Luer tip is inserted into the catheter hub 102. As shown, the one or more slots 510 intersect the groove 124 having the proximal shoulder 172 and distal shoulder 174.

Figure 5C:
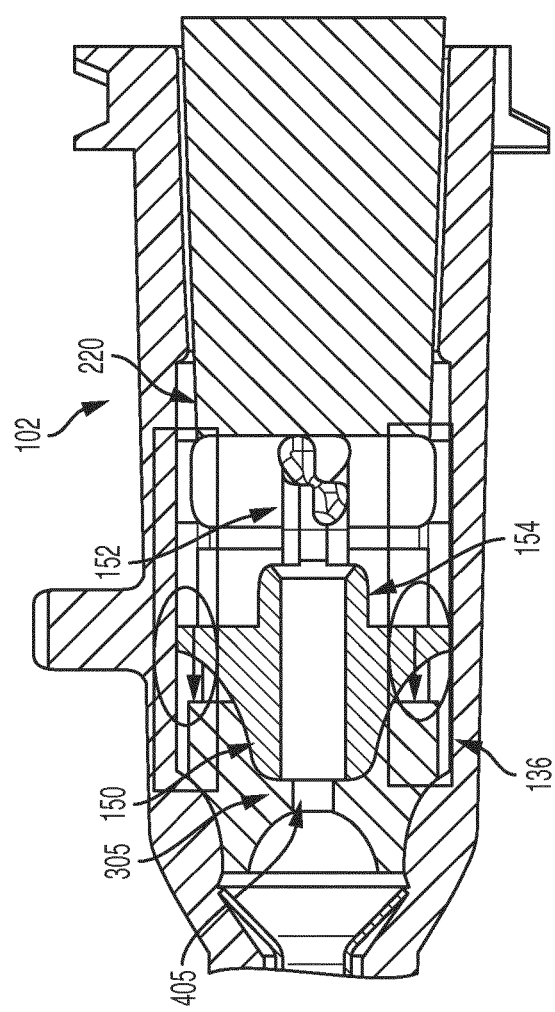
FIG. 5C is a schematic cross-sectional side view of the catheter assembly of FIG. 1 in which the catheter hub is now connected with a male Luer and the valve actuator is advanced by the male Luer to push open the valve.

With reference now to FIG. 5C, the catheter hub 102 is shown with a male medical implement 220, shown schematically only, positioned in the proximal opening thereof but not completely advanced in the distal direction into the interior of the catheter hub, indicated by the actuator 150 still not pushed into the valve disc to open the valve disc. The male medical implement 220 can have a threaded collar for threaded engagement with the exterior threads on the catheter hub. The threaded collar can be fixed to the male tip or be rotatable relative to the male tip. The male medical implement or instrument 220 can be a male Luer, a syringe tip, an IV set connector, or other male tip having a Luer taper. For example, the male medical implement can be connected to an IV tubing, which is connected to an IV fluid source for fluid delivery through the male medical implement 220, the catheter hub 102, and the catheter tubing 104 to deliver fluid therapy to a patient.

When initially inserting the male medical implement 220, herein male tip, into the proximal opening of the catheter hub 102, the male tip initially contacts the two plunger elements 152 on the valve opener 150 to advance a distally directed force on the two plunger elements 152 to move the activation end 315 at the nose section distally forward into the valve 136 to open the valve. The arc cross section of each of the plunger elements 152 can have a smaller diameter than the inside diameter of the catheter hub 102 to provide a larger overlapping contact surface for the distal end of the male medical instrument 220 to push against, as previously discussed. This can also be designed to contact the inside wall of the catheter hub at a tangential point. This arrangement can avoid the relatively thin plunger elements from being missed by the advancing male tip and wedging between the male medical instrument 220 and the inside wall of the catheter hub 102. However, as shown in FIGS. 3A-3C, the outward protrusions 335 on the two plunger elements 152 of the actuator 150 have ample proximal surfaces 325 that are configured to be abutted by the male Luer tip without missing or misaligning.

Figure 5D:
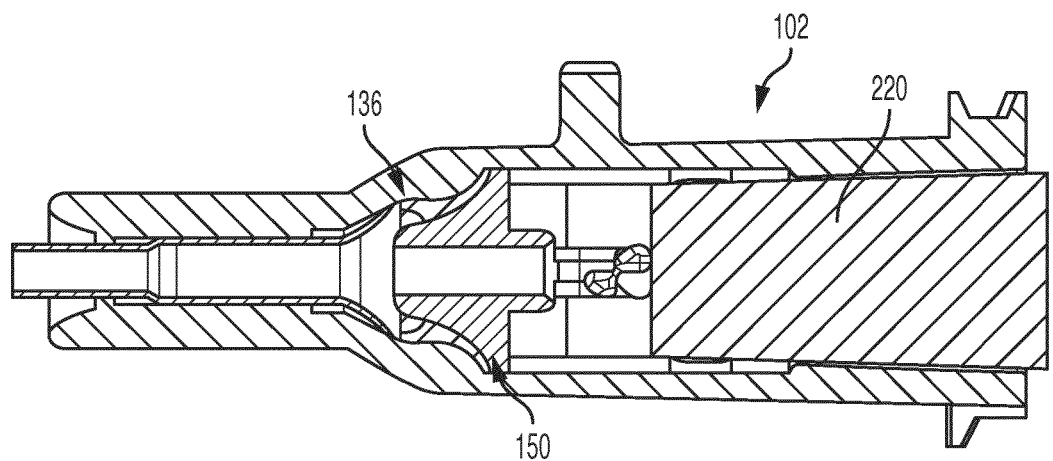
FIG. 5D is a schematic cross-sectional side view of the catheter assembly of FIG. 1 in which the catheter hub is now connected with a male Luer and the valve actuator is advanced distally to push open the valve.

The distally directed force moves the valve opener 150 in the distal direction until the geometries of the male tip 220 and the proximal opening of the catheter hub stop further distal advancement of the male tip, which is shown in FIG. 5D. In an example, a female Luer taper of the catheter hub 102 and a male Luer taper of the male tip 220 register and block distal advancement of the male tip further into the opening of the catheter hub. A seal is provided by the Luer engagement to prevent fluid from leaking out the proximal opening of the catheter hub.

As the valve opener 150 moves distally by the distal advancement of the male tip 220, the activation end 315 of the actuator is urged distally and pushes against the proximally facing surface the valve disc 50 of the valve 136. In particular, the activation end 315 of the valve opener 150 initially pushes against the proximally facing surface of the valve disc 50. For example, the activation end 315 contacts and pushes on the proximally facing wall surface of the valve disc 50, causing the valve slit 405, or valve slits if more than one, on the valve disc to open. The valve body 402 is axially fixed, such as abutted against a distal shoulder or stepped surface 164 provided in the distal bore section 145 of the interior cavity 130 of the catheter hub, and only the flaps of the valve disc 50 deflect distally forward when pushed by the actuator to open the valve. In some examples, depending on the elasticity or rigidity of the valve body, the valve disc compresses between the tapered surface of the actuator and the interior wall surfaces of the catheter hub to open the slit for fluid flow.

Once the valve 136 is opened, fluid from the male tip 220 can then flow through the catheter hub 102, through the valve 136, and through the lumen of the catheter tube 104.

Alternatively, a suction can be generated by the male medical instrument, such as a syringe or vacuum blood collection tube, and blood aspirated from the patient. This is often done for testing samples before infusion therapy is commenced. Also, typically any remaining blood can first be flushed from the inside of the catheter hub 102 before infusion therapy is commenced.

Figure 5E:
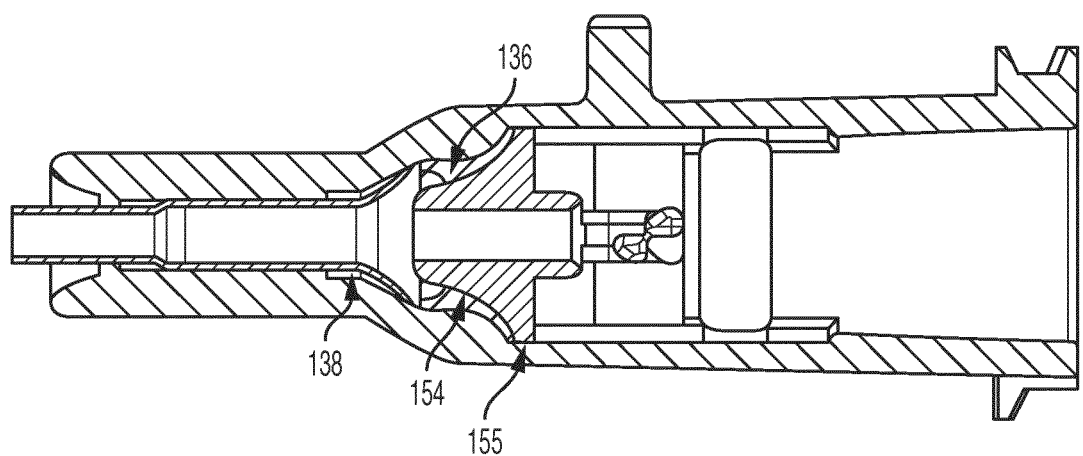
FIG. 5E is a schematic cross-sectional side view of the catheter assembly of FIG. 1 in which the valve actuator is advanced to compress the valve into a fully-open position with the male Luer tip removed.

FIG. 5E illustrates the valve 136 in a fully open position after the Luer tip in FIG. 5C has been fully inserted and then removed. The valve 136 can be made of a pliable material, such as an elastomer, that is configured to deform and compress between the actuator 154, the interior surface of the catheter hub and possibly part of the bushing 138, as show in FIG. 5D. In an embodiment, the actuator 154 is configured to remain attached to the valve, in the distally forward position, even after the Luer tip is removed. For example, the guiding arms 155 of the actuator can engage undercuts or grooves (not shown) on the interior catheter surface to lock the actuator 154 into the forward position. In another example, the guiding arms 155 retain the actuator in the forward position due to frictional bias against the interior catheter hub surface. In still other examples, the compressive force generated by the tapered section 161 of the rigid body of the actuator is greater than the recovery force generated by the resilient properties of the valve such that the valve actuator remains in the distally forward position even after the male tip is removed. In some examples, a biasing member, such as a helical spring or an elastomeric ring, may be placed distally of the valve, such as between the bushing and the valve, to assist the flaps in returning to their uncompressed or un-deflected state to close the one or more slits after removal of the male metal instrument or implement.

With reference again to FIGS. 3A-3C, 5C and 5D, when the male Luer tip advances the actuator 150 in the distal direction, the distal end surface of the male Luer tip pushes against the proximal surfaces or abutting surfaces 325 of the two outward protrusions 335. In an example, the proximal surfaces 325 are not orthogonal to the lengthwise axis of the actuator so that when pushed by the planar surface of the male Luer tip, the contact causes the two elongated elements 152, to which the two outward protrusions are attached, to deflect radially inwardly towards one another or outwardly away from one another until the flat distal end of the male Luer tip seats flush with the abutting surfaces 325. Alternatively or additionally thereto, as the two outward protrusions 335 move distally forward within the groove 124 inside the interior cavity of the catheter hub, the two outward protrusions 335 contact the distal shoulder 174, the geometry of which causes the two outward protrusions to deflect radially inwardly, which causes the two elongated elements 152 to deflect radially inwardly towards one another.

In an example, the radial inward deflection of the two elongated elements 152 towards one another during distal displacement allow the actuator to move an axial distance that is greater than the length measured between the proximal shoulder 172 and the distal shoulder 174 of the groove 124. In other words, the deflection provides clearance for the actuator to move in the distal direction. The deflection between the outward protrusions 335 on the two leg extensions or elongated elements 152 and the distal shoulder 174 of the groove 124 enables the actuator 150, hence the male Luer tip, to move distally until the male Luer tip and the female Luer of the catheter hub register. Thus, even if the outward protrusions 335 contact the distal shoulder 174 prior to the two Luer surfaces register or seat, the male Luer tip can still advance distally until seated within the female Luer as the elongated elements 152 can deflect radially inwardly when pushed against the distal shoulder 174.

Upon removal of the male Luer tip, the actuator 150 remains engaged to the valve and the one or more slits of the valve are opened by the activation end of the actuator while the two elongated elements 152 can un-flex and return to their more natural state, which includes moving away from one another, or can remain inwardly deflected if being constrained by the distal shoulder 174 or other surfaces within the catheter hub. In still other examples, the valve can have sufficient elasticity and the valve opener, such as the activation end of the valve opener, can be sized and shaped to allow the flaps to uncoil and for the valve opener to be pushed in the proximal direction by the valve to close the flaps from fluid flow. To again open the valve, the male Luer tip can be re-inserted into the catheter hub to advance the valve opener into the valve to open the flaps.

Thus, an aspect of the present disclosure is understood to include a catheter assembly comprising a valve 136 with a valve body and wherein a valve perimeter of the valve body can seat within a bore section of the catheter hub at a stepped surface. Therefore, a catheter hub with a singularly formed hub body 102a may be used with the present catheter assembly. Thus, the size of the catheter hub 102, such as the outer diameter or dimension of the catheter hub, can be reduced compared to one that utilizes a two-part hub body. The two-part hub body where they join along a seam can thus be reduced to provide a catheter assembly with a relatively smaller outer profile.

A still yet further aspect of the present disclosure is understood to include a valve opener 150 for opening the valve 136. The valve opener 150 is configured to push the valve against another structure, such as the bushing 138 or against a stepped surface inside the catheter hub. The valve opener can have nose section 161 with an activation end 315 and wherein the activation end and at least part of the nose section are located inside a bore of the valve in a ready to use position, prior to activation. The nose section of the actuator and the bore of the valve can have a size-on-size fit. In an example, the nose section has a frusto-conical shape and the bore of the valve has an inverse frusto-conical surface.

In a yet further aspect of the present disclosure, the actuator comprises one or more elongated elements, such as two elongated elements or more than two, extending in the proximal direction relative to the nose section. For example, two elongated elements can extend from the body section of the actuator and each having a fixed end attached to the body section and a free end that is free to independently deflect or move. Each of the two free ends can deflect radially inwardly when activated by a male medical implement during activation of the valve. Each of the two elongated elements can also have bumps configured to engage a tip protector or needle guard.

The body section of the actuator can have a surface defining a bore having two open ends. The surface can be continuous or can have slots or grooves to define flow channels. The body section of the actuator can have an outer diameter having a first dimension and the two elongated legs can define and outer profile or diameter having a second dimension and wherein the second dimension is larger than the first dimension.

One or more guiding arms can extend radially from the body section of the actuator. Each guiding arm can seat within a corresponding slot formed inside the interior cavity of the catheter hub. The slot can angularly align the actuator so that the actuator does not rotate.

In a still further aspect of the present disclosure, a catheter assembly is provided comprising a valve, a valve opener, a needle hub with a needle, and a catheter hub with a catheter tube. The valve assembly can further include a tip protector for blocking the needle tip in a needle protective position. Following successful venipuncture, a male tip, such as a male Luer, can be inserted into a proximal opening of the catheter hub to advance the valve opener in a distal direction and open the valve. The valve, the valve opener, the needle hub, and tip protector can have structural features disclosed elsewhere herein. For example, the actuator can have two leg extensions and wherein the two leg extensions can flex radially when pushed in a direction by a male medical implement.

Figure 6B:
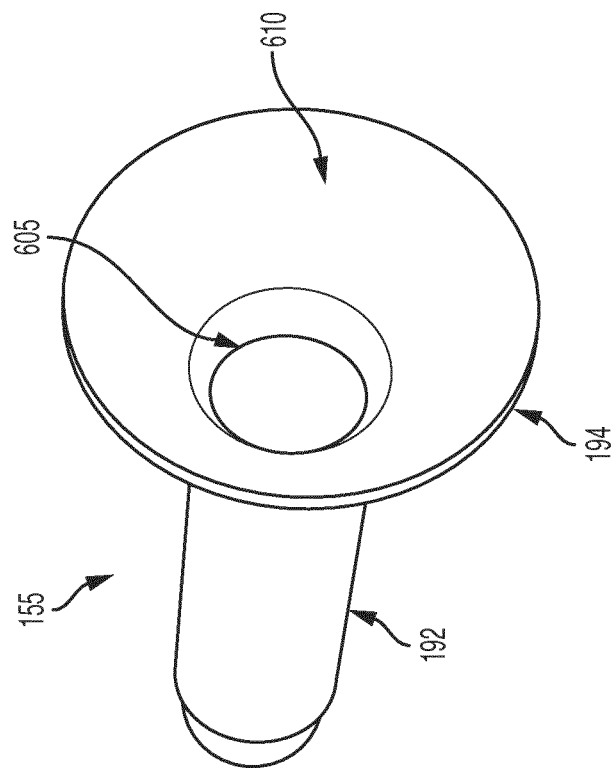
FIGS. 6A-6B illustrate a side view and proximal perspective view of the bushing of FIG. 2.
Figure 6A:
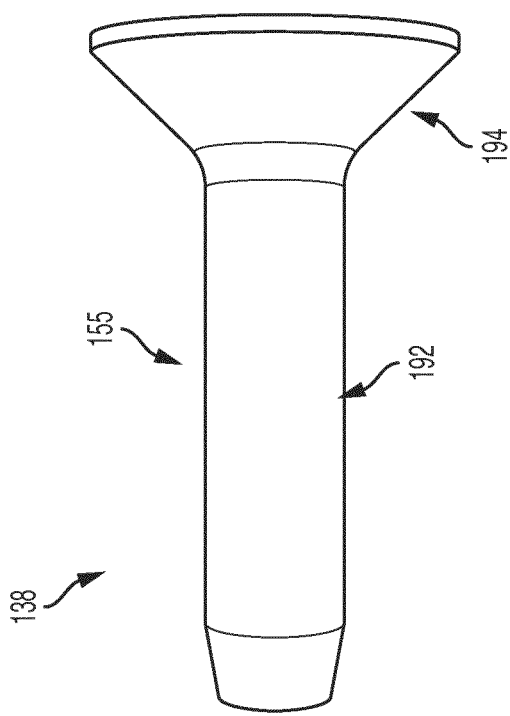

FIG. 6A illustrates a side view of the bushing 138 of FIG. 2 and FIG. 6B shows a proximal perspective view of the same bushing. The bushing 138 comprises a first body section 192 and a second body section 194 extending from the first body section 192 having a cone shape. The first body section 192 can have an elongated body that can have a cylindrical shape with an optional tapered distal tip or nose section. The bushing 138 defines a passage 605 through which the needle passes. The valve 136 (not shown) can be positioned adjacent the proximal end of the second body section 194 and may directly abut the proximal end and/or the interior surface 610 of the second body section 194. In some embodiments, there may be a small space between the valve 136 and the proximal interior surface 610 or the proximal end of the second body section, at least while the catheter assembly 100 is in the ready to use position.

Figure 7:
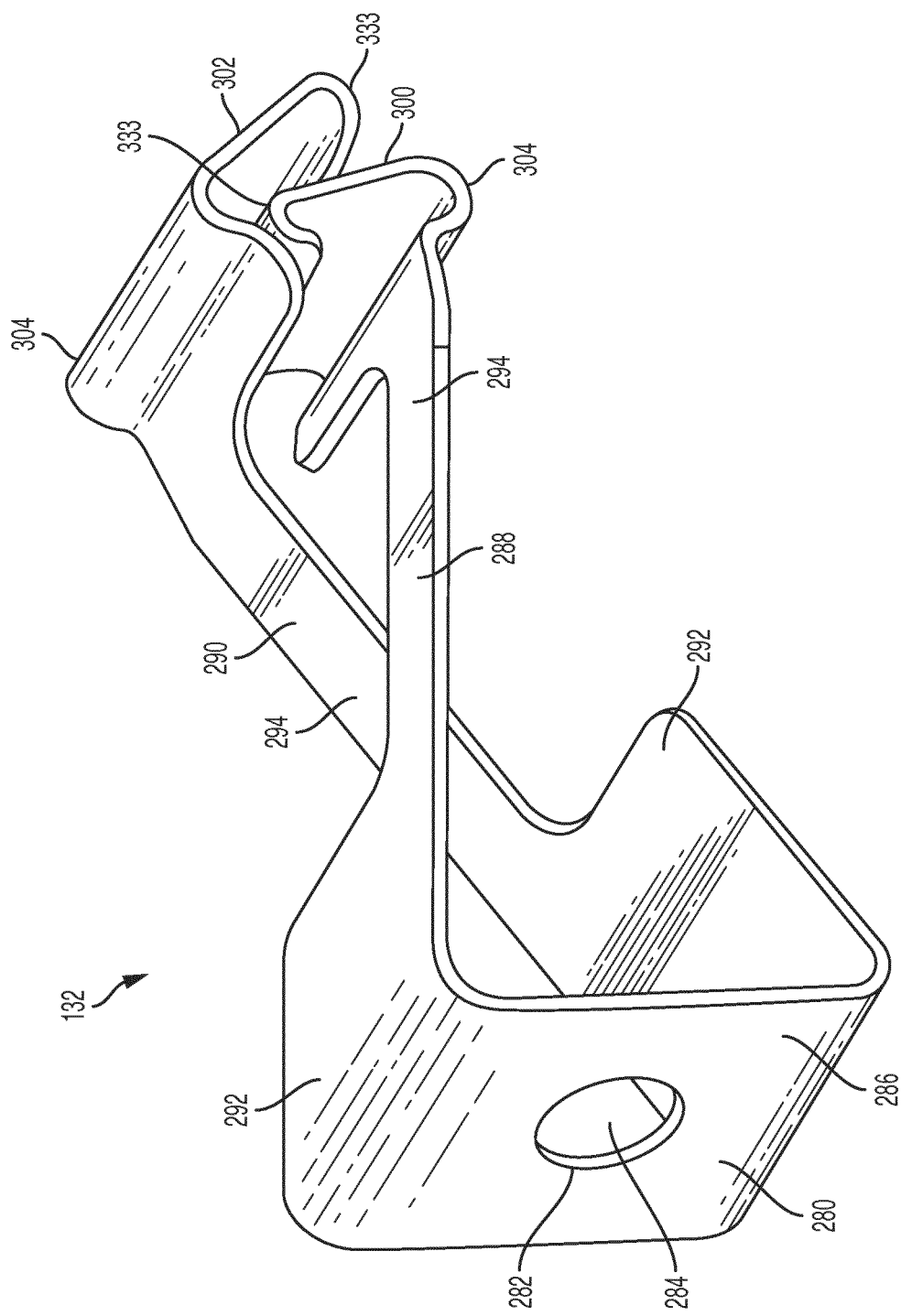
FIG. 7 is a rear isometric view of the needle guard 132 of FIG. 1.

FIG. 7 is a rear isometric view of the needle guard 132 of FIG. 1. The needle guard 132 is exemplary only as needle guards with other or different features may be used instead of the exact needle guard 132 shown in FIG. 7. In the present embodiment, the needle guard 132 comprises a proximal wall 280 comprising a perimeter 282 defining an opening 284. The proximal wall 280 has a proximally facing wall surface 286 and a distally facing wall surface opposing the proximally facing wall surface. At least one resilient arm 288 extends distally of the proximal wall 280. As shown, two resilient arms 288, 290 extend distally of the proximal wall. One arm can be longer than the other arm. Each arm can also include different arm widths, including a first arm section 292 of a first width and a second arm section 294 of a second width, which is smaller than the first width. The two arms can originate from different ends of the proximal wall 280 and can cross one another at their respective second arm sections 294. Thus, when viewed from a side along the lengthwise direction of the needle guard 132, the two arms can intersect one another. When used with a needle, the two arms 288, 290 intersect one another when in a ready to use position and when in the protective position. In an alternative embodiment, the two arms 288, 290 can originate from different ends of the proximal wall and extend in a distal direction without crossing one another. Thus, the two arms 288, 290 can also have essentially the same arm width along the length of each respective arm.

A distal wall 300, 302 is provided at an end of each arm 288, 290. The distal walls 300, 302 can overlap one another along an axial direction of the needle guard by utilizing different arm lengths and/or angling one of the walls at an intersection 304 between the distal wall and the resilient arm. The intersection 304 of each arm can also be referred to as an elbow. In an example, the intersection 304 of each arm, if two arms are utilized, can engage an interior of the catheter hub to removably secure the needle guard within the catheter hub in the ready position and during the transition process of removing the needle 108 from the catheter hub 102. Alternatively, the one or two elbows 304 can be biased radially outwardly to contact or engage a ring or groove inside the catheter hub. As discussed above, the ends 333 of the two distal walls 300, 302 can optionally rest on bumps 330 formed on an actuator 150 in a ready to use position without the distal walls 300, 302 or the arms 288, 290 engaging the catheter hub in a ready to use position. By resting the arms on the bump or bumps 330, drag between the needle guard and the needle can be eliminated or reduced. The needle guard 132 may be folded from a stamped metal sheet to form the guard as shown. Ribs may be formed on the arms, the proximal wall, and/or the distal walls to increase structurally rigidity.

FIGS. 8A-8G illustrate various embodiments of the actuator. The bumps described herein can be unitarily formed with the plunger element or plunger elements or separately formed and subsequently added to the plunger element or plunger elements. The plunger elements of the actuators can each include an outward protrusion or radial tab with surfaces sized and shaped for contact by a male medical implement.

Figure 8A:
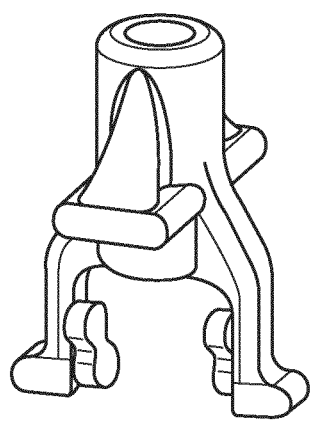
FIGS. 8A-8G illustrate various different embodiments of the actuator.

FIG. 8A illustrates an actuator embodiment having two pairs of bumps formed on opposite plunger elements. Each pair of bumps can comprise a first bump and a second bump. The two bumps can be positioned along different planes or elevations to define two different surfaces for supporting two different ends on two different arms of a needle guard. For example, two bumps, one from each of the two pairs, can support an end 333 of one distal wall of a needle guard and the other two bumps can support an end 333 of the other distal wall. The two bumps for supporting a first arm of a needle guard can be positioned further proximally than the two bumps for supporting a second arm of the needle guard.

Figure 8B:
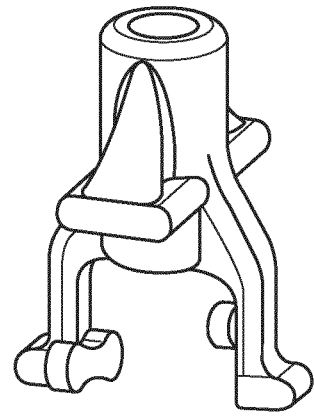

FIG. 8B illustrates an actuator embodiment having a single bump on alternating sides of opposing plunger elements and staggered in the axial direction. One bump on a first plunger element can support one end 333 of a distal wall and the other bump on a second plunger element can support the other end 333 of the second distal wall so that the two bumps, one on each plunger element, are configured to support the two ends of the two distal walls.

Figure 8C:
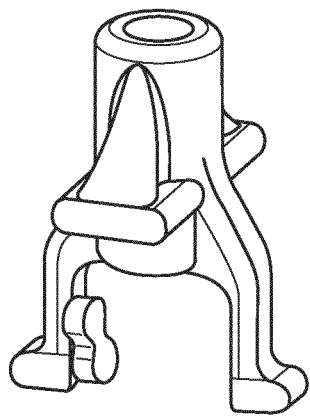

FIG. 8C illustrates an actuator embodiment having two bumps, such as a pair of bumps, on one plunger element, with no bumps on the opposite plunger element of an actuator with two plunger elements. The pair of bumps on only one plunger element can be located or positioned on two different planes or levels so that each bump of the pair of bumps can support a different end 333 of the needle guard having two distal walls with two ends. In operation, the arms of the tip protector would engage on only one side of the actuator, such as on only one plunger element, with the pair of bumps. One bump can support one end 333 of a distal wall so that the two bumps on one plunger element are configured to support the two ends of the two distal walls of the needle guard, one end on each distal wall.

Figure 8D:
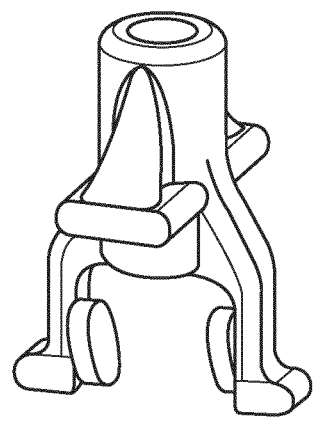

FIG. 8D illustrates an actuator embodiment having a single solid bump extending diagonally on each opposing plunger element. The single bump can extend substantially across the plunger element such that the single bump on each plunger element can engage both ends on the two distal walls of the first arm and of the second arm, such that each of the two ends of the two distal walls contact the same bump on each plunger element. In other words, if a centerline can be drawn through each single bump, the centerline is angled so that first ends of the centerlines of the two bumps support one end of an arm of a needle guard and second ends of the centerlines of the two bumps support the other end of the other arm of the needle guard.

Figure 8E:
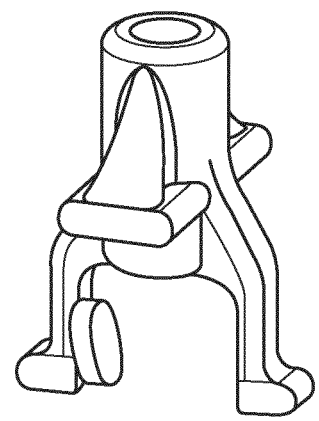

FIG. 8E illustrates an actuator embodiment having a single solid bump extending diagonally on one plunger element, with no bump on the opposite plunger element. The bump of FIG. 8E is similar to the bumps of FIG. 8D, but wherein one of the plunger elements does not utilize a bump.

Figure 8F:
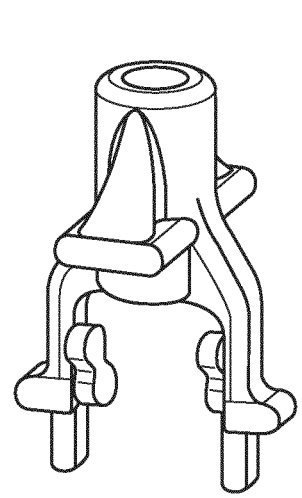

FIG. 8F illustrates an actuator embodiment that can represent any of the actuator elements described elsewhere herein but wherein each leg extension has an extended plunger element or a plunger extension. The two extended plunger elements, one on each plunger element, can extend the overall length of the actuator. Thus, the present actuator element is better suited for longer length catheter hubs. As shown, a plunger extension, which can have a bar or a polygonal shaped length, is provided on each plunger element to extend the overall length of each plunger element.

Figure 8G:
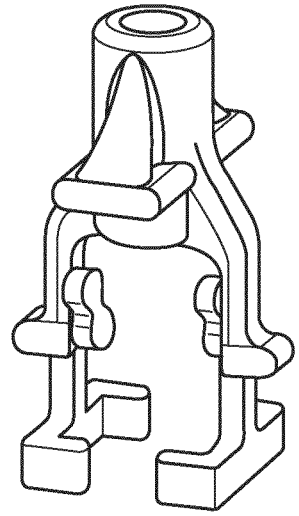

FIG. 8G illustrates an actuator embodiment that can represent any of the actuator elements described elsewhere herein but wherein each leg extension has an extended plunger element or plunger extension and wherein each plunger extension has additional protrusions. Each plunger extension can have a proximal end with two radial extensions or projections that increase the surface area at the end of the plunger extension. Thus, the two plunger extensions can have four radial extensions, two on each plunger extension, to engage with various Luer tips inserted into the catheter hub to advance the actuator.

The actuators of FIGS. 8F and 8G can also include external bumps formed on an outer surface of each elongated element as well as on the inner surface of each elongated element. The external bumps can be sized and shaped to contact proximal and distal shoulders of a groove inside a catheter hub. The overall length of the various valve actuators described herein, hence the one or more plunger elements on each valve actuator, can be selected so that insertion of a male Luer tip into the female Luer of a catheter hub is sufficient to push against the proximal end of the valve actuator to axially move the valve actuator into the valve to open the one or more flaps of the valve for fluid flow.

Figure 9A:
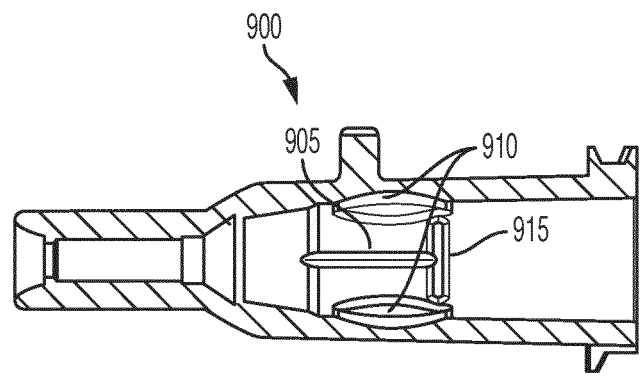
FIG. 9A illustrates an alternate embodiment of the catheter hub.
Figure 9B:
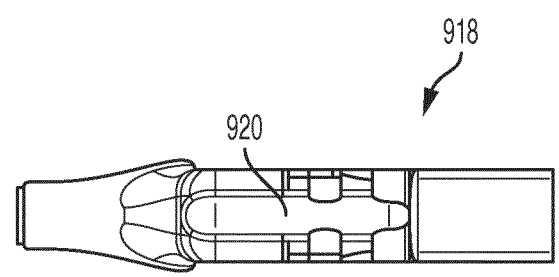
FIGS. 9B-9D illustrate another alternate embodiment configured to engage with catheter hub of FIG. 9A.
Figure 9C:
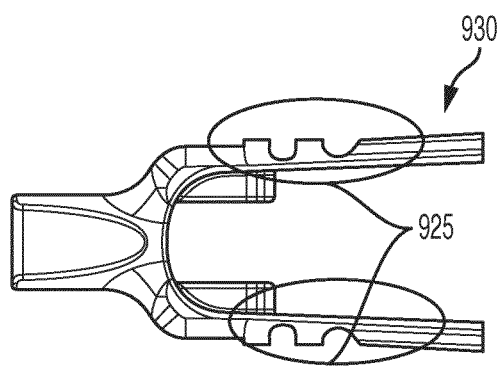
Figure 9D:
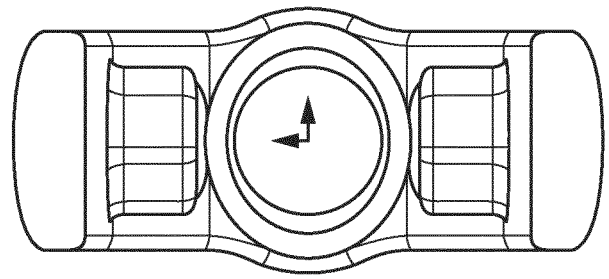

FIGS. 9A-9D illustrate alternate embodiments of a catheter hub and an actuator. FIG. 9A illustrates a catheter hub 900 having one or more ribs 905 formed on the interior surface. FIGS. 9B-9D illustrate side, top and proximal views, respectively, of an embodiment of an actuator having one or more slots 920 and one or more undercuts 925 formed on one or more plunger elements 930. The ribs 905 of the catheter hub 900 are configured to engage with the slots 920 formed on the actuator 918 to provide an anti-rotation feature that reduces or eliminates rotation of the actuator. The voids 910 formed on the interior surface of the catheter hub 900 aid in the seating of a needle protector. The bumps 915 can engage with undercuts 925 on the actuator 918 to help hold the actuator in place.

Figure 9E:
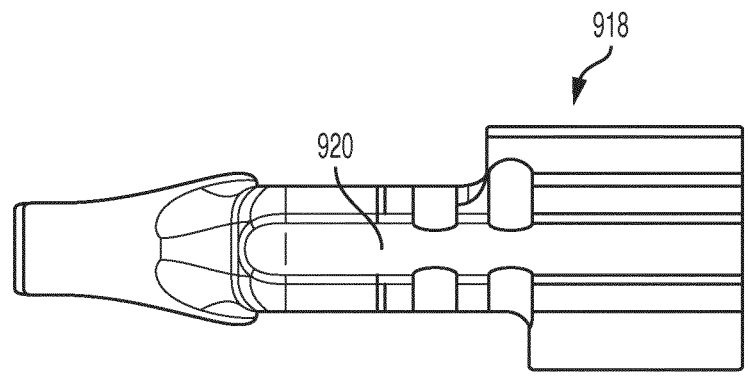
FIGS. 9E-9G illustrate another alternate embodiment of the actuator configured to engage with catheter hub of FIG. 9A.
Figure 9F:
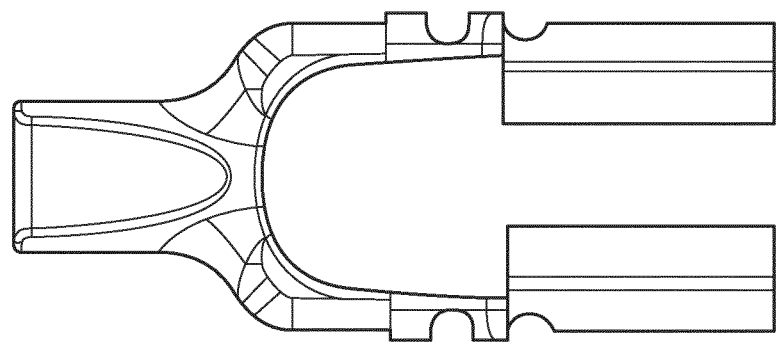
Figure 9G:
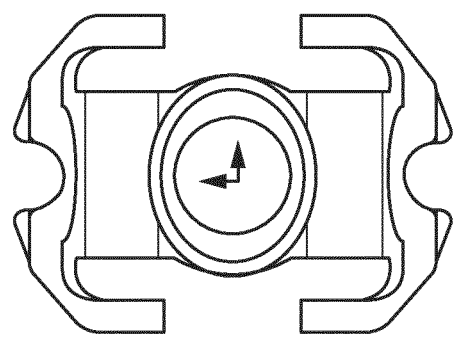

FIGS. 9E-9G illustrate another embodiment of an actuator similar to the actuator of FIGS. 9B-9D, but having relatively wider plunger elements that have a greater surface area for engaging with a Luer tip. In some embodiments, the length of the plunger elements are extended or shortened to accommodate various lengths catheter hubs.

Methods of making and of using the catheter assemblies and their components described elsewhere herein are within the scope of the present disclosure.

Although limited embodiments of catheter assemblies and their components have been specifically described and illustrated herein, many modifications and variations will be apparent to those skilled in the art. For example, the needle guard may be of one piece or can be integrated from more than one piece, such as from multiple pieces. Furthermore, it is understood and contemplated that features specifically discussed for one catheter assembly or for one component may be adopted for inclusion with another catheter assembly or another component, provided the functions are compatible. Accordingly, it is to be understood that the catheter assemblies and their components constructed according to principles of the disclosed devices, systems, and methods may be embodied other than as specifically described herein. The valve and valve opener described herein can also be used with a needle hub by locating them inside a female Luer taper of the needle hub. The valve and valve opener can also be used in the female connector of an infusion needle or a blood collection device or a central venous catheter or peripherally inserted central catheter (PICC). In other words, the valve and valve opener can be used in any medical device intended for infusion or bodily fluid collection with a female Luer housing or hub. The disclosure is also defined in the following claims.

What is claimed is:

1. A needle assembly comprising:
    a needle hub with a needle extending from a distal end of the needle hub;
    a catheter hub having an interior surface defining an interior cavity;
    a catheter tube attached to the catheter hub and having the needle extending through the catheter tube and having a needle tip extending out a distal opening of the catheter tube in a ready to use position;
    a valve positioned in the interior cavity of the catheter hub, said valve comprising a valve body having an outer perimeter positioned in a bore section of the catheter hub, a proximal receptacle on a proximal end, a distal receptacle on a distal end, and a valve disc located between the proximal receptacle and distal receptacle;
    an actuator positioned in the interior cavity of the catheter hub, the actuator is configured to open the valve, the actuator comprising:

a body having a nose section and an activation end, the activation end is located within the proximal receptacle and is configured to push the valve disc to open the valve; and an extension leg on a proximal end of the actuator, the extension leg having an engagement section with a support surface extending radially of a surface of the extension leg, the support surface configured for supporting;

a safety clip having a proximal wall, a proximal opening on the proximal wall, a resilient arm, and an end;

wherein the end of the resilient arm is supported by the support surface of the engagement section when the safety clip is in the interior cavity of the catheter hub in the ready to use position.

2. The needle assembly of claim 1, wherein the engagement section with the support surface is a radially extending tab formed on the extension leg located in an undercut formed on the interior surface of the catheter hub, the location of the radially extending tab in the undercut prevents dislodgement of the actuator from within the interior cavity of the catheter hub.

3. The needle assembly of claim 2, wherein the undercut has a proximal shoulder and a distal shoulder and wherein the radially extending tab is located closer to the proximal shoulder than the distal shoulder in the ready to use position.

4. The needle assembly of claim 1, wherein the actuator further comprises:
one or more guide arms extending radially from the body of the actuator, the one or more guide arms configured to engage one or more slots on the interior surface of the catheter hub, the engagement between the one or more guide arms and the one or more slots configured to prevent rotation of the actuator within the catheter hub.

5. The needle assembly of claim 1, wherein the actuator further comprises:
a second extension leg on the proximal end of the actuator spaced from the extension leg, the second extension leg having a second engagement section for supporting the safety clip.

6. The needle assembly of claim 5, wherein the actuator further comprises:
a third engagement section formed on the extension leg near the engagement section and a fourth engagement section formed on the second extension leg near the second engagement section.

7. The needle assembly of claim 6, wherein the engagement section is formed opposite the second engagement section and the third engagement section is formed opposite the fourth engagement section.

8. The needle assembly of claim 7, wherein the engagement section and the fourth engagement section are configured to engage with the resilient arm of the safety clip and the second engagement section and third engagement section are configured to engage with a second arm of the safety clip, wherein the resilient arm and second arm of the safety clip have different lengths.

9. The needle assembly of claim 5, wherein the extension leg and the second extension leg each has an arc shape cross section.

10. The needle assembly of claim 1, wherein the extension leg is a first extension leg and wherein the engagement section is formed on an inner surface of the first extension leg and a second engagement section is formed on an inner surface of a second extension leg, diagonally to the engagement section.

11. The needle assembly of claim 1, wherein the support surface for supporting has a bump; the bump being diagonally formed to have different planes on an interior surface of the extension leg.

12. The needle assembly of claim 1, wherein the proximal receptacle of the valve is defined by an inverse frusto-conical shape.

13. The needle assembly of claim 1, wherein the distal receptacle of the valve is defined by a dome shape.

14. A method of manufacturing a needle assembly comprising:
providing a catheter hub with a catheter tube with a distal opening, said catheter hub comprising a hub body defining an interior cavity and a proximal opening;
positioning a bushing inside the catheter hub and against the catheter tube and positioning a valve proximal of the bushing; the valve comprising a valve body having a distal valve section and a proximal valve section defining a proximal receptacle, and wherein the distal valve section is located in a bore section of the interior cavity and the bore section contacts the distal valve section to secure the valve inside the interior cavity;
positioning a valve opener adjacent the valve and inside the interior cavity of the catheter hub so that a nose section of the valve opener is located inside the proximal receptacle, the valve opener comprising an extension leg on a proximal end of the valve opener, the extension leg having an engagement section;
positioning a safety clip in the interior cavity of the catheter hub so that an end of an arm of the safety clip is located over the engagement section, the engagement section having a surface to support the safety clip when the safety clip is in the interior cavity of the catheter hub;
placing a needle, which is attached to a needle hub, through the catheter hub, the valve, the valve opener, the safety clip and the catheter tube so that a tip of the needle extends out the distal opening of the catheter tube.

15. The method of claim 14, further comprising locating a guiding arm extending from the valve opener in a slot form in the interior cavity of the catheter hub to prevent rotation of the valve opener.

16. The method of claim 14, further comprising providing a radially extending tab on the extension leg spaced from the engagement section; said radially extending tab having a planar surface.

17. The method of claim 14, further comprising providing a second extension leg comprising a second engagement section and a second radially extending tab, wherein said radially extending tab on the extension leg and said second radially extending tab on the second extension leg provide surfaces for a male Luer tip to push against to open the valve.

18. The method of claim 17, wherein the extension leg and the second extension leg move radially when surfaces of the radially extending tab and second radially extending tab are pushed by a male Luer tip.

19. The method of claim 17, wherein the extension leg and the second extension leg each have a shoulder near the nose section that form an arc shape along a width of the actuator.

20. The method of claim 17, wherein the valve opener is configured to remain attached and keep the valve open even after the male Luer tip is removed and does not contact the surfaces of the radially extending tab and the second radially extending tab.

21. The method of claim 14, wherein the surface of the engagement section is defined by a bump for the supporting of the safety clip;
the bump being diagonally formed to have different planes on an interior surface of the extension leg.

22. The method of claim 14, wherein the proximal receptacle of the valve is defined by an inverse frusto-conical shape.

23. A needle assembly comprising:
a needle hub with a needle extending from a distal end of the needle hub;
a catheter hub having an interior surface defining an interior cavity;
a catheter tube attached to the catheter hub and having the needle extending through the catheter tube and having a needle tip extending out a distal opening of the catheter tube in a ready to use position;
a valve positioned in the interior cavity of the catheter hub, said valve comprising a valve body having an outer perimeter positioned in a bore section of the catheter hub, a proximal receptacle on a proximal end, a distal receptacle on a distal end, and a valve disc located between the proximal receptacle and distal receptacle;
an actuator positioned in the interior cavity of the catheter hub, the actuator is configured to open the valve, the actuator comprising:
a body having a nose section and an activation end, the activation end is located within the proximal receptacle and is configured to push the valve disc to open the valve;
an extension leg on a proximal end of the actuator, the extension leg having an engagement section having a surface for supporting; and
a radially extending tab formed on the extension leg located in an undercut formed on the interior surface of the catheter hub, the location of the radially extending tab in the undercut prevents dislodgement of the actuator from within the interior cavity of the catheter hub;
a safety clip having a proximal wall, a proximal opening on the proximal wall, a resilient arm, and an end;
wherein the end of the arm is supported by the surface of the engagement section when the safety clip is in the interior cavity of the catheter hub in the ready to use position.

24. The needle assembly of claim 23, wherein the undercut has a proximal shoulder and a distal shoulder and wherein the radially extending tab is located closer to the proximal shoulder than the distal shoulder in the ready to use position.

25. The needle assembly of claim 23, wherein the actuator further comprises:
one or more guide arms extending radially from the body of the actuator, the one or more guide arms configured to engage one or more slots on the interior surface of the catheter hub, the engagement between the one or more guide arms and the one or more slots configured to prevent rotation of the actuator within the catheter hub.

\* \* \* \* \*